(12) United States Patent
Minai et al.

(10) Patent No.: US 8,740,777 B2
(45) Date of Patent: Jun. 3, 2014

(54) IN-VIVO IMAGING SYSTEM AND BODY-INSERTABLE APPARATUS

(75) Inventors: Tetsuo Minai, Hachioji (JP); Shinsuke Tanaka, Hino (JP); Akio Uchiyama, Yokohama (JP)

(73) Assignee: Olympus Medical Systems Corp., Tokyo (JP)

( * ) Notice: Subject to any disclaimer, the term of this patent is extended or adjusted under 35 U.S.C. 154(b) by 195 days.

(21) Appl. No.: 12/917,863

(22) Filed: Nov. 2, 2010

(65) Prior Publication Data

US 2011/0213203 A1 Sep. 1, 2011

Related U.S. Application Data

(63) Continuation of application No. PCT/JP2010/058065, filed on May 12, 2010.

(30) Foreign Application Priority Data

May 12, 2009 (JP) ................................. 2009-115576

(51) Int. Cl.
*A61B 1/06* (2006.01)
*A61B 1/04* (2006.01)

(52) U.S. Cl.
USPC ............................ 600/160; 600/178; 600/109

(58) Field of Classification Search
CPC ............ A61B 1/05; A61B 1/07; A61B 1/043; A61B 1/045; A61B 1/0638; A61B 1/0669; A61B 1/00096; A61B 5/0084; A61B 5/0071
USPC ................... 600/109, 160, 178, 180; 362/587
See application file for complete search history.

(56) References Cited

U.S. PATENT DOCUMENTS

| 2001/0017649 A1* | 8/2001 | Yaron .............................. 348/45 |
| 2002/0103417 A1* | 8/2002 | Gazdzinski ................... 600/109 |
| 2003/0028078 A1* | 2/2003 | Glukhovsky .................. 600/109 |
| 2004/0054255 A1* | 3/2004 | Pilgrim et al. ................ 600/109 |

(Continued)

FOREIGN PATENT DOCUMENTS

| EP | 1 880 657 A1 | 1/2008 |
| JP | 63-167577 | 7/1988 |

(Continued)

OTHER PUBLICATIONS

Abstract of Japanese Patent Publication No. 10-020214, dated Jan. 23, 1998.

(Continued)

*Primary Examiner* — Philip R Smith
*Assistant Examiner* — William Chou
(74) *Attorney, Agent, or Firm* — Scully, Scott, Murphy & Presser, P.C.

(57) ABSTRACT

A body-insertable apparatus includes a light-receiving unit that includes light-receiving elements each having a receiving wavelength spectrum; light-emitting units including a near ultraviolet light source and including a yellow light source; a selection unit that can select, from among the light-emitting units, light-emitting units corresponding respectively to the near ultraviolet and the yellow light sources; an image creating unit creating a normal-light image or creating a special-light image; a transmitting unit transmitting the normal-light image or the created special-light image; and a control unit controlling driving of the light-receiving elements in accordance with selection performed by the selection unit.

7 Claims, 28 Drawing Sheets

(56) References Cited

U.S. PATENT DOCUMENTS

| | | | |
|---|---|---|---|
| 2005/0215911 A1* | 9/2005 | Alfano et al. | 600/476 |
| 2006/0036131 A1* | 2/2006 | Glukhovsky et al. | 600/160 |
| 2006/0251408 A1* | 11/2006 | Konno et al. | 396/14 |
| 2008/0068664 A1* | 3/2008 | Gilad | 358/302 |
| 2008/0177140 A1 | 7/2008 | Cline et al. | |
| 2008/0208297 A1* | 8/2008 | Gertner et al. | 607/92 |
| 2008/0234548 A1* | 9/2008 | Amit | 600/160 |
| 2009/0091614 A1 | 4/2009 | Gono et al. | |
| 2009/0216079 A1* | 8/2009 | Morgan et al. | 600/109 |
| 2010/0032546 A1* | 2/2010 | Kawano et al. | 250/205 |
| 2010/0254153 A1* | 10/2010 | Hama et al. | 362/551 |
| 2012/0262052 A1* | 10/2012 | Oshio | 313/483 |

FOREIGN PATENT DOCUMENTS

| | | |
|---|---|---|
| JP | 2002-369217 | 12/2002 |
| JP | 2003-070728 | 3/2003 |
| JP | 2003-325438 | 11/2003 |
| JP | 2005-074034 | 3/2005 |
| JP | 2005-198794 | 7/2005 |
| JP | 2005-319115 | 11/2005 |
| JP | 2006-136453 | 6/2006 |
| JP | 2006-166940 | 6/2006 |
| JP | 2006-314629 | 11/2006 |
| JP | 2006-345947 | 12/2006 |
| JP | 3898781 | 1/2007 |
| JP | 2007-212376 | 8/2007 |
| JP | 2007-525261 | 9/2007 |
| JP | 2008-086759 | 4/2008 |
| JP | 2008-096413 | 4/2008 |
| JP | 2008-118635 | 5/2008 |
| JP | 2009-544470 | 12/2009 |
| WO | WO 2007/108270 A1 | 9/2007 |
| WO | WO 2008/011255 A3 | 1/2008 |

OTHER PUBLICATIONS

Abstract of International Publication No. WO 2008/011255 A2, dated Jan. 24, 2008.

International Search Report dated Jun. 15, 2010.

Extended Supplementary European Search Report dated Jul. 17, 2012 from related application EP 10774944.2-2319.

* cited by examiner

IN-VIVO IMAGING SYSTEM AND BODY-INSERTABLE APPARATUS

CROSS-REFERENCE TO RELATED APPLICATIONS

This application is a continuation of PCT international application Ser. No. PCT/JP2010/058065 filed on May 12, 2010 which designates the United States, incorporated herein by reference. This application also claims the benefit of Japanese Application No. 2009-115576 filed in Japan on May 12, 2009.

BACKGROUND OF THE INVENTION

1. Field of the Invention

The present invention relates to an in-vivo imaging system and a body-insertable apparatus.

2. Description of the Related Art

Of apparatuses that are conventionally used to observe inside human or animal subjects, there are endoscopes having two ends with one end thereof being inserted into the subject to observe inside the subject (hereinafter, simply referred to as an "endoscope") and capsule-shaped endoscopes (hereinafter, simply referred to as a "capsule endoscope"). Examples of endoscopes include electronic endoscopes that have, for example, a charge coupled device (CCD) sensor or a complementary metal oxide semiconductor (CMOS) at the distal end thereof and also include fiberscopes having a tube probe through which a bundle of optical fibers is inserted. With such an endoscope, images of the inside of the subject are acquired by inserting the probe through, for example, the mouth or the anus of the subject (see, for example, Japanese Patent No. 3898781).

In contrast, a capsule endoscope is a capsule-shaped body-insertable apparatus that is inserted into the subject, and whose size is such that it can be swallowed by humans or animals. Such a capsule endoscope is inserted, for example, orally into the subject. The capsule endoscope that is inserted into the subject captures, for example, periodically, an image inside the subject and sends, to an external receiving device, the captured image from inside the subject as a wireless signal (see, for example, Japanese Laid-open Patent Publication No. 2003-70728). An observer replays, one by one or continuously, multiple images obtained using the endoscope or the capsule endoscope and observes the images, thereby observing inside the subject.

In endoscopes, white light sources, such as halogen lamps, are used for light sources for illuminating inside the subject. Furthermore, in endoscopes, an image-capturing mechanism that uses a frame sequential color filter method is used and in which a monochrome CCD and rotating color filters are used for the image-capturing mechanism. White light sources, such as halogen lamps can generally emit, in a visible light band, light of substantially uniform intensity. With the image-capturing mechanism using the frame sequential color filter method, by conforming to the transmittances of the light of each filter for the three primary colors (R, G, and B), it is possible to easily obtain a uniform light receiving sensitivity for each color component. Accordingly, by using a white light source and an image-capturing mechanism that uses the frame sequential color filter method, it is possible to obtain a clear and well-balanced image for each color component.

However, white light sources, such as halogen lamps, and an image-capturing mechanism using the frame sequential color filter method have a relatively large structure and also require a relatively large amount of electrical power. Accordingly, it is difficult to install, in a capsule endoscope having a size limit, the white light source and the image-capturing mechanism described above. Therefore, with conventional capsule endoscopes, light emitting diodes (LED) that are relatively small in size and whose electrical power consumption is relatively small are used as light sources. Furthermore, with conventional capsule endoscopes, CCD arrays that include a receiving element for each of the three primary colors are used as imaging units.

Japanese Laid-open Patent Publication No. 2002-369217 discloses a technology in which, when an LED and a CCD array are used, by positioning the center wavelength of an emission spectrum of the LED between the main spectral sensitivities of each CCD, the color or luminance of the captured image are brought closer to the original color of the object.

However, in recent years, due to the diversification of observation, required capsule endoscopes are those capable of acquiring, in addition to an image obtained when the image is captured using a white light (hereinafter, referred to as a "normal-light image" or a "white light image"), an image obtained when the image is irradiated with light having a certain wavelength (hereinafter, referred to as a "special light") (hereinafter, referred to as a "special-light image").

Accordingly, in recent years, there have been capsule endoscopes in which color filters are arranged in light-receiving units, such as CCDs. However, with such capsule endoscopes, each light-receiving unit for RGB color components has an arch-shaped receiving wavelength spectrum. Accordingly, if light having a flat-shaped emission wavelength spectrum is incident, for each color component, on the light-receiving unit having the arch-shaped receiving wavelength spectrum, there may be a case in which receiving wavelength spectra that are combined (a combined receiving wavelength spectrum) are not flat-shaped spectra. As a result, in some cases, a normal-light image obtained using the capsule endoscope may not be an image that is accurately captured.

Furthermore, when using the technology disclosed in, for example, Japanese Laid-open Patent Publication No. 2005-74034, although a normal-light image can be obtained, in order to obtain a special-light image, a process is required, for example, in which a specific wavelength component is extracted from the normal-light image. This increases the burden imposed on the image processing. Furthermore, in Japanese Laid-open Patent Publication No. 2005-74034 described above, because special-light images are not considered, it is not possible to obtain, except for normal-light images, the special-light images.

SUMMARY OF THE INVENTION

An in-vivo image-capturing system according to an aspect of the present invention includes a body-insertable apparatus that is introduced into a subject; and a receiving device that receives a wireless signal transmitted from the body-insertable apparatus. The body-insertable apparatus includes a light-receiving unit that includes a plurality of light-receiving elements each having a receiving wavelength spectrum; a plurality of light-emitting units having a plurality of emission wavelength spectra, the light-emitting units including a near ultraviolet light source whose peak of the emission intensity is near ultraviolet light with a wavelength deviated, from an emission wavelength spectrum that is associated with the receiving wavelength spectrum, by a predetermined wavelength and including a yellow light source whose peak of the emission intensity is yellow; a selection unit that can select, from among the light-emitting units, a light-emitting unit corresponding to the near ultraviolet light source and a light-emitting unit corresponding to the yellow light source; an image creating unit that creates a normal-light image in accordance with a combined flat-shaped wavelength spectrum combined using the light-receiving unit or that creates a special-light image in accordance with a combined sharp wavelength spectrum combined using a pixel that receives blue-color-component light of the light-receiving unit and a pixel that receives green-color-component light of the light-receiving unit, the light being obtained at the emission of light when the near ultraviolet light source and the yellow light source are selected using the selection unit; a transmitting unit that transmits the normal-light image or the special-light image created by the image creating unit; and a control unit that controls driving of the light-receiving elements in accordance with selection performed by the selection unit.

A body-insertable apparatus according to another aspect of the present invention includes a light-receiving unit that includes a plurality of light-receiving elements each having a receiving wavelength spectrum; a plurality of light-emitting units having a plurality of emission wavelength spectra, the light-emitting units including a near ultraviolet light source whose peak of the emission intensity is near ultraviolet light with a wavelength deviated, from a receiving wavelength spectrum that is associated with the receiving wavelength spectrum, by a predetermined wavelength and including a yellow light source whose peak of the emission intensity is yellow; a selection unit that can select, from among the light-emitting units, a light-emitting unit corresponding to the near ultraviolet light source and a light-emitting unit corresponding to the yellow light source; an image creating unit that creates a normal-light image in accordance with a combined flat-shaped wavelength spectrum combined using the light-receiving unit or that creates a special-light image in accordance with a combined sharp wavelength spectrum combined using a pixel that receives blue-color-component light of the light-receiving unit and a pixel that receives green-color-component light of the light-receiving unit, the light being obtained at the emission of light when the near ultraviolet light source and the yellow light source are selected using the selection unit; a transmitting unit that transmits the normal-light image or the special-light image created by the image creating unit; and a control unit that controls driving of the light-receiving elements in accordance with selection performed by the selection unit.

The above and other features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Figure 1:
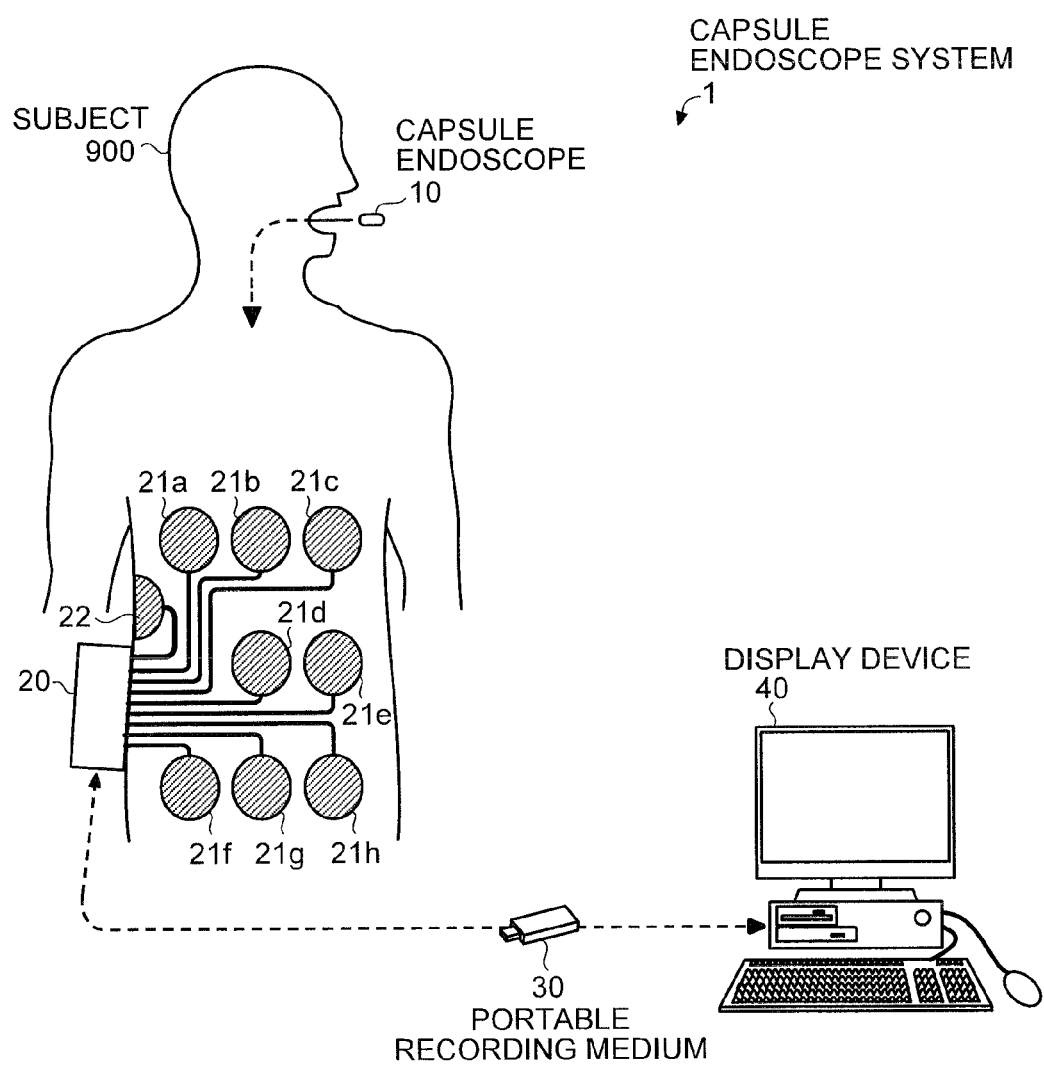
FIG. 1 is a schematic diagram illustrating, in outline, the configuration of a capsule endoscope system according to a first embodiment of the present invention.

In the following, preferred embodiments according to the present invention will be described in detail with reference to the accompanying drawings. In the drawings used for the following description, shapes, sizes, and positional relationships are only schematically illustrated so that the content of the present invention can be understood. Accordingly, the present invention is not limited to only the shapes, the sizes, and the positional relationships illustrated in the drawings. Furthermore, in the drawings, to make the configuration clear, the hatching of certain cross sections has been omitted. Furthermore, numerical values described later are mentioned as only preferable examples of the present invention; therefore, the present invention is not limited to those numerical values.

First Embodiment

In the following, an in-vivo observation system and a body-insertable apparatus according to a first embodiment of the present invention will be described with reference to the drawings. In the following description, as the in-vivo observation system, a capsule endoscope system 1 like that illustrated in FIG. 1 is used as an example, in which a capsule endoscope 10 that is orally introduced into the subject and that acquires images inside the subject by performing an image capturing operation while moving inside the lumen, through the esophagus to the anus, of the subject is used as a body-insertable apparatus. The capsule endoscope 10 is a monocular capsule endoscope that includes a single imaging unit; however, it is not limited thereto. For example, a pantoscopic capsule endoscope can also be used. Furthermore, various types thereof can be used; for example, a monocular or pantoscopic capsule endoscope that is orally introduced into the subject and that floats on the liquid retained in the stomach, the small intestine, or the large intestine of the subject can also be used as the body-insertable apparatus.

Configuration

FIG. 1 is a schematic diagram illustrating, in outline, the configuration of the capsule endoscope system 1 according to the first embodiment of the present invention. As illustrated in FIG. 1, the capsule endoscope system 1 includes the capsule endoscope 10 that is orally introduced into a subject 900; a receiving device 20 that receives, from the capsule endoscope 10, image data that is wirelessly transmitted; and a display device 40 that is used to input, via, for example, a portable recording medium 30, the image data received by the receiving device 20, and that is used to display the data. At least one of receiving antennas 21a to 21h (hereinafter, from among the receiving antennas 21a to 21h, reference numeral 21 denotes a given antenna) that is used to receive a signal wirelessly transmitted from the capsule endoscope 10 is attached on the surface of the subject 900. The receiving antenna 21 is connected to the receiving device 20 via, for example, a signal cable and a balun (not shown). If a control signal or the like is wirelessly input to the capsule endoscope 10, for example, a transmitting antenna 22 that is used for wireless transmission and is connected, via the balun or the like, can also be attached to the receiving device 20 on the surface of the subject 900.

Capsule Endoscope

Figure 2:
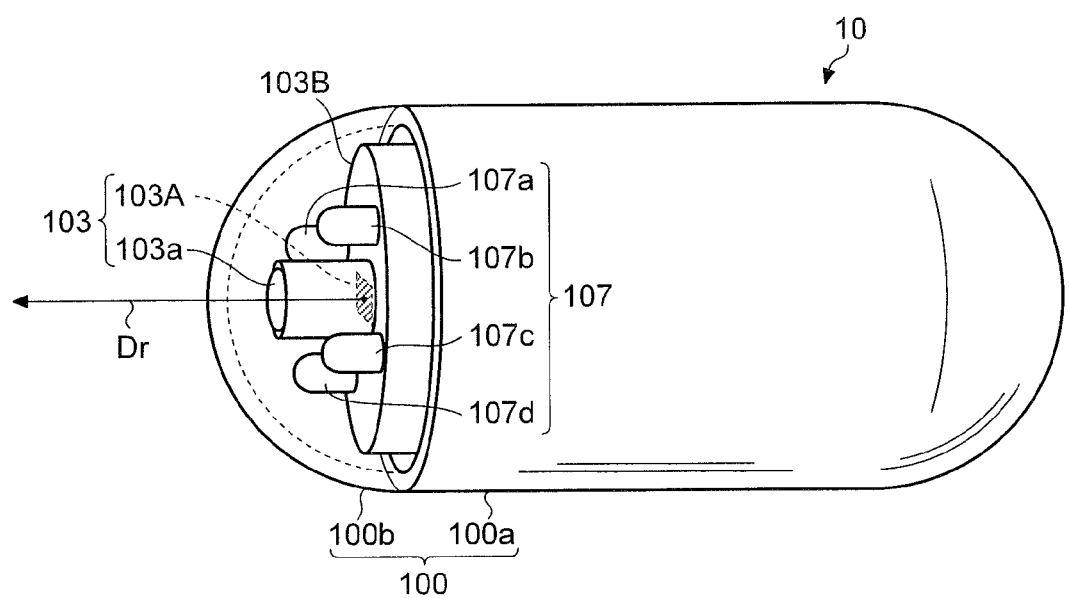
FIG. 2 is a perspective view illustrating, in outline, the configuration of a capsule endoscope according to the first embodiment of the present invention.
Figure 3:
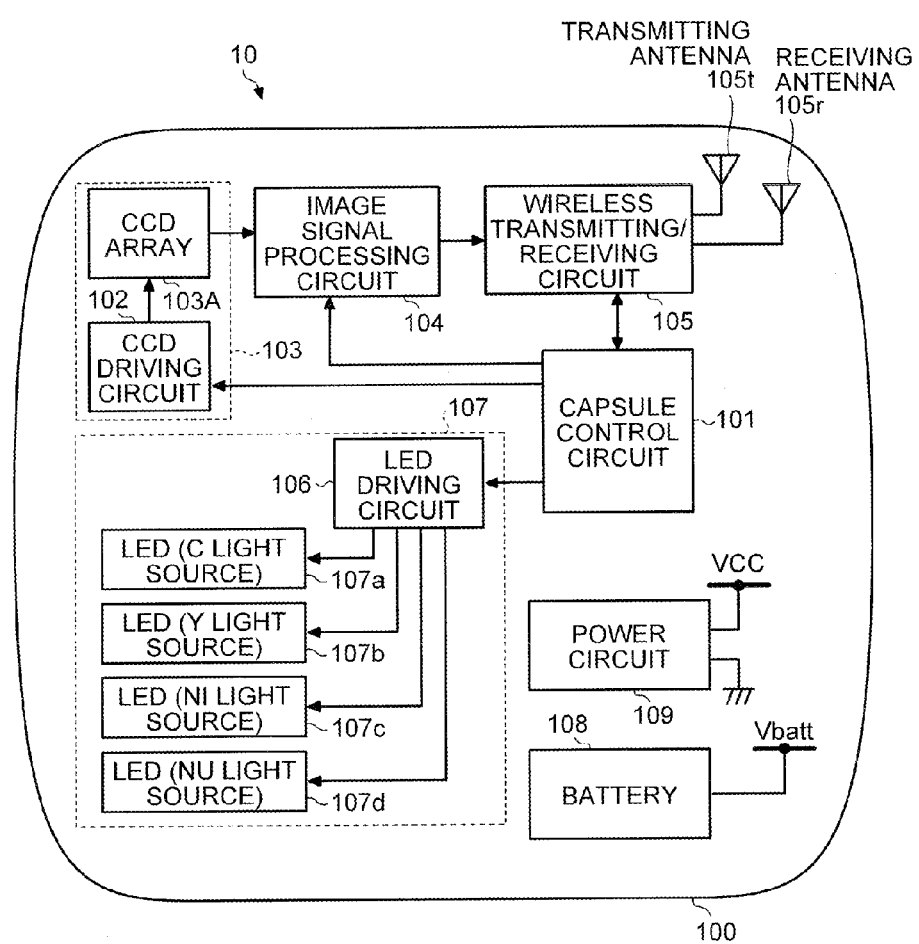
FIG. 3 is a block diagram illustrating, in outline, the configuration of the capsule endoscope according to the first embodiment of the present invention.

In the following, the configuration of the capsule endoscope 10 according to the first embodiment of the present invention will be described with reference to the drawings. FIG. 2 is a perspective view illustrating, in outline, the configuration of the capsule endoscope 10 according to the first embodiment of the present invention. FIG. 3 is a block diagram illustrating, in outline, the configuration of the capsule endoscope 10 according to the first embodiment of the present invention.

As illustrated in FIG. 2, the capsule endoscope 10 includes a casing 100 that has a hollow cylindrical portion 100a with one end thereof being opened and the other end thereof being closed in a dome shape and that has a dome-shaped transparent cap 100b that is arranged at the opened end of the cylindrical portion 100a. Because the transparent cap 100b is fitted into an opening of the cylindrical portion 100a, the inside of the casing 100 is sealed in a liquid-tight manner. A substrate 103B is arranged on the transparent cap 100b side in the casing 100 with the mounting surface of the substrate 103B facing towards the transparent cap 100b side. On the mounting surface of the substrate 103B, for example, the following are arranged: LEDs 107a to 107d, functioning as a illumination unit 107, that illuminate inside the subject 900; an objective lens 103a that is included in an imaging unit 103 that captures images inside the subject 900; and a CCD array 103A. With this configuration, the illumination direction and the image-capturing direction Dr of the imaging unit 103 and the illumination unit 107 are oriented towards the outside of the casing 100 via the transparent cap 100b.

As illustrated in FIG. 3, the capsule endoscope 10 includes, in the casing 100, a capsule control circuit 101; the imaging unit 103 that includes a CCD driving circuit 102 and the CCD array 103A; an image signal processing circuit 104; a wireless transmitting/receiving circuit 105; the illumination unit 107 that includes an LED driving circuit 106 and the LEDs 107a to 107d; a battery 108; and a power circuit 109, both of which supply electrical power to each circuit in the capsule endoscope 10.

Figure 4:
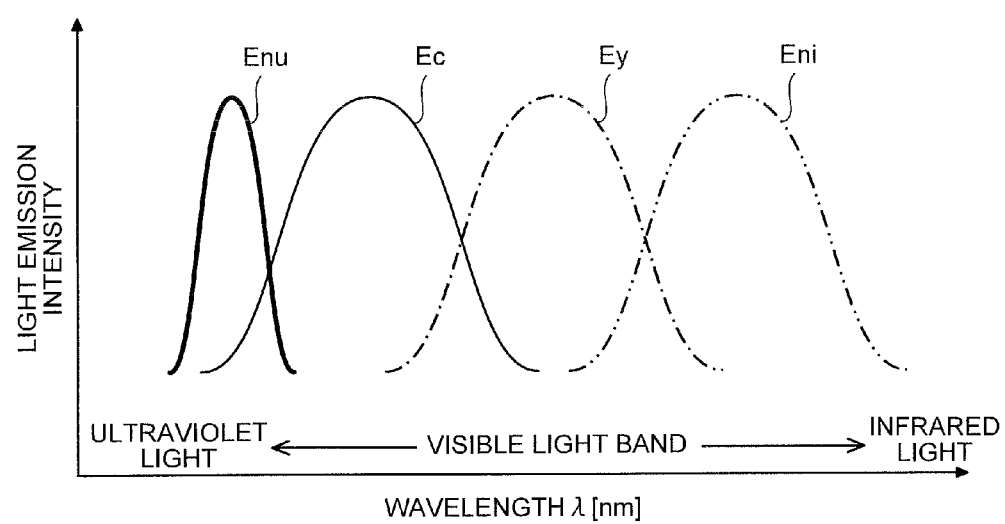
FIG. 4 is a schematic diagram illustrating emission spectra of each LED in an illumination unit in the capsule endoscope according to the first embodiment of the present invention.

In the illumination unit 107 according to the first embodiment of the present invention, the LED 107a is a cyan (C) light source, the LED 107b is a yellow (Y) light source, the LED 107c is a near infrared light source (NI), and the LED 107d is a near ultraviolet light source (NU). FIG. 4 is a schematic diagram illustrating emission spectra of each of the LEDs 107a to 107d in the illumination unit 107 in the capsule endoscope 10.

As illustrated in FIG. 4, an emission spectrum Ec of the LED 107a corresponding to a C light source, an emission spectrum Ey of the LED 107b corresponding to a Y light source, and an emission spectrum Eni of the LED 107c corresponding to a near infrared light source have substantially the same spectral shape both in light emission intensity and bandwidth. Furthermore, for the emission spectra Ec, Ey, and Eni, in order to obtain substantially uniform light intensity over the entire visible light band, a wavelength indicating each emission intensity peak (or an emission center wavelength) is shifted.

For example, the wavelength (or the center wavelength) indicating the intensity peak of the emission spectrum Ec of the LED 107a corresponding to the C light source is located on the most ultraviolet light side from among the emission spectra Ec, Ey, and Eni of the three light sources (LEDs 107a to 107c). The wavelength (or the center wavelength) indicating the intensity peak of the emission spectrum Eni of the LED 107c corresponding to the near infrared-ray (NI) light source is located on the most infrared light side from among the emission spectra Ec, Ey, and Eni of the three light sources (LEDs 107a to 107c). The emission spectrum Ey of the LED 107b corresponding to the Y light source is located substantially midpoint between the wavelength (or the center wavelength) indicating the intensity peak of the emission spectrum Ec and the wavelength (or the center wavelength) indicating the intensity peak of the emission spectrum Eni. This makes it possible for the illumination unit 107 to obtain substantially uniform light intensity over the entire visible light band.

The shape of the emission spectrums Ec, Ey, and Eni is not limited to that illustrated in FIG. 4. Modifications are possible as long as a combination of emission spectra is used in which substantially uniform light intensity can be obtained over the entire visible light band, or, CCDs (103r, 103g, and 103b) for each color component (R,G,B) can implement substantially the same spectral sensitivity characteristic. Furthermore, the LED 107c corresponding to the near infrared light source can be replaced by a magenta (M) light source.

In contrast, the bandwidth of the emission spectrum Enu of the LED 107d corresponding to the near ultraviolet light (NU) light source is narrower than the bandwidths of the emission spectra Ec, Ey, and Eni of the LEDs 107a to 107c. In the first embodiment of the present invention, the LED 107d is a light source for obtaining a special-light image. Accordingly, by making the bandwidth of the emission spectrum Enu of the LED 107d narrower than the bandwidth of other light sources, a clear image can be obtained for color components in the vicinity of the near ultraviolet light that corresponds to illumination light. However, the bandwidth is not limited thereto. For example, the bandwidth of the emission spectrum Enu of the LED 107d can be the same as that of the emission spectra (Ec, Ey, and Eni) of the other light sources (LEDs 107a to 107c).

Furthermore, regarding the total light intensity distribution obtained when the LEDs 107a to 107d simultaneously emit light, it is preferable that the light intensity preferably decrease between a light intensity distribution of the wavelength band that is mainly made up of near ultraviolet light (hereinafter, referred to as "special light") emitted from the LED 107d and a light intensity distribution of the wavelength band that is mainly made up of combined light emitted from the LEDs 107a to 107c. By doing so, the spectrum of the near ultraviolet light (hereinafter, referred to as "special light") emitted from the LED 107d can be practically separated from the spectrum of the combined light emitted from the LEDs 107a to 107c. As a result, it is possible to make a special-light image, which is obtained using special light as illumination light, clearer.

Figure 5:
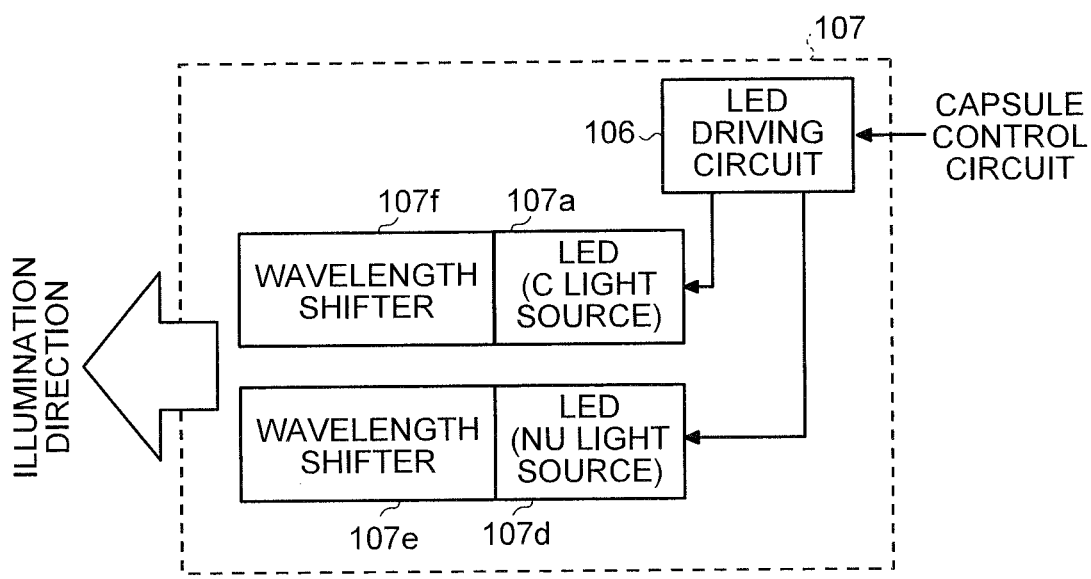
FIG. 5 is a block diagram illustrating, in outline, the configuration of another type of illumination unit according to the first embodiment of the present invention.

Furthermore, it is also possible to replace the emission spectrum Ey by light of a yellow (Y) component spectrum that is obtained by performing wavelength conversion on a part of the near ultraviolet light from the LED 107d using a wavelength converter, such as fluorescent material. The LED 107d and the LED 107b are driven for an overlapping period of time during the normal and special light observations. Accordingly, as illustrated in FIG. 5, the LED 107b can be eliminated by arranging, at the LED 107d, a wavelength shifter 107e that converts a part of the near ultraviolet light from the LED 107d to light of a spectrum equal to the yellow light from the LED 107b. As a result, the configuration of the illumination unit 107 can be simplified. FIG. 5 is a block diagram illustrating, in outline, the configuration of another type of illumination unit 107 according to the first embodiment of the present invention.

Furthermore, in a similar manner as described in the above, it is also possible to replace the emission spectrum Eni by light of a near infrared light (NI) component spectrum that is obtained by performing wavelength conversion on a part of the cyan light emitted from the LED 107a using the wavelength converter, such as the fluorescent material. The LEDs 107a to 107d are driven for an overlapping period of time during the normal observation. Accordingly, in addition to the wavelength shifter 107e that converts a part of the near ultraviolet light emitted from the LED 107d to light of a spectrum equal to the yellow light emitted from the LED 107b, as illustrated in FIG. 5, by arranging a wavelength shifter 107f that converts a part of the cyan light emitted from the LED 107a to light of a spectrum equal to the near infrared light emitted from the LED 107c, both the LED 107b and the LED 107c can be eliminated. As a result, the configuration of the illumination unit 107 can further be simplified.

However, the wavelength shifters 107e and 107f described above are not limited thereto. For example, it is also possible to use one or more wavelength shifters that convert the near ultraviolet light emitted from the LED 107d to light of the spectral shape of each of the emission spectra Ec, Ey, and Eni.

A description will be given by referring back to FIG. 3. In FIG. 3, the imaging unit 103 includes the CCD array 103A corresponding to an image-capturing device in which CCDs functioning as photoelectric conversion elements are arranged in a two-dimensional matrix. The imaging unit 103 also includes the CCD driving circuit 102 that drives, under the control of the capsule control circuit 101, the CCD array 103A. Furthermore, the imaging unit 103 includes, for example, the substrate 103B and the objective lens 103a illustrated in FIG. 2.

Figure 6:
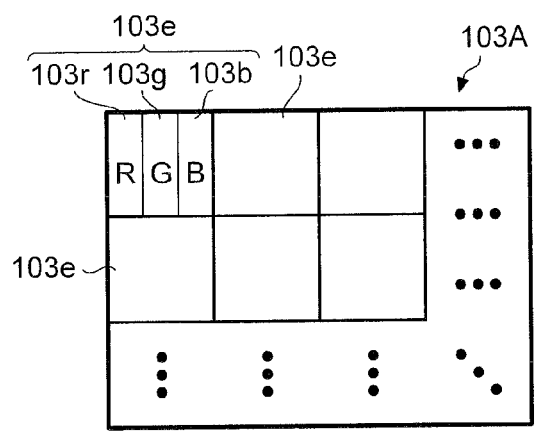
FIG. 6 is a schematic diagram illustrating an example configuration of a CCD array according to the first embodiment of the present invention.
Figure 7:
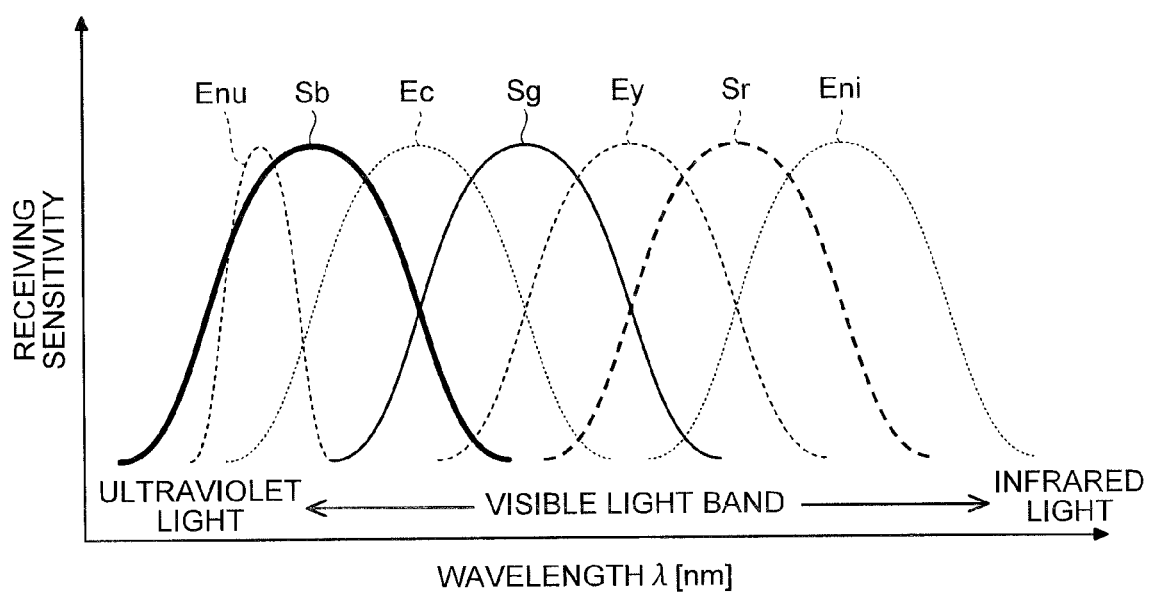
FIG. 7 is a schematic diagram illustrating spectra of spectral sensitivity characteristics of each CCD according to the first embodiment of the present invention.
Figure 8:
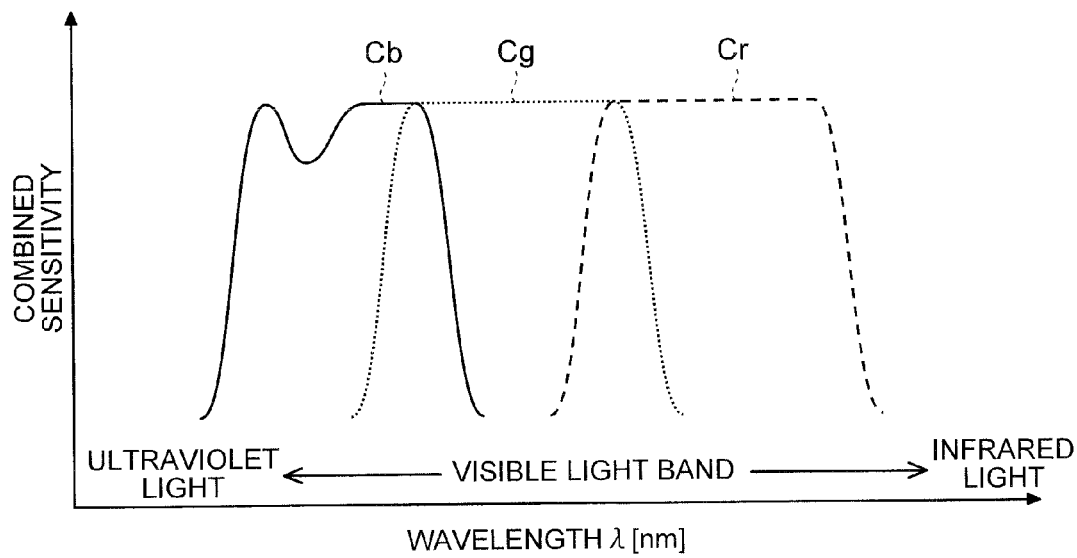
FIG. 8 is a schematic diagram illustrating spectra of combined sensitivity characteristics of each CCD obtained when all of the LEDs according to the first embodiment of the present invention emit light.
Figure 9:
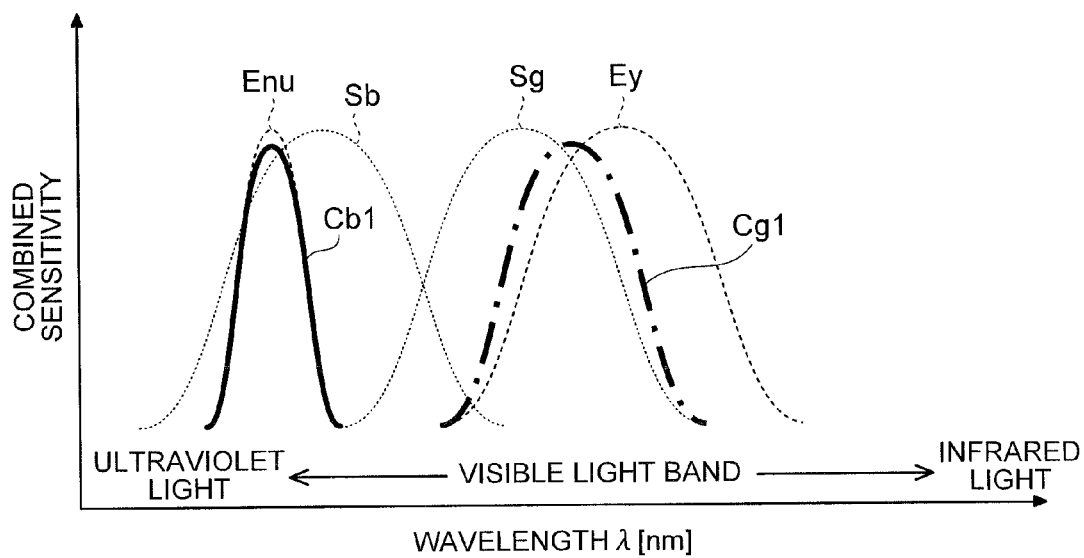
FIG. 9 is a schematic diagram illustrating spectra of combined sensitivity characteristics of a B-pixel CCD and a G-pixel CCD obtained when an LED, which is an NU light source, and an LED, which is a Y light source, are driven in the first embodiment of the present invention.

FIG. 6 is a schematic diagram illustrating an example configuration of the CCD array 103A according to the first embodiment of the present invention. FIG. 7 is a schematic diagram illustrating spectra Sr, Sg, and Sb of spectral sensitivity characteristics of CCDs 103r, 103g, and 103b. FIG. 8 is a schematic diagram illustrating spectra Cr, Cg, and Cb of combined sensitivity characteristics of each of the CCDs 103r, 103g, and 103b obtained when all of the LEDs 107a to 107d emit light. FIG. 9 is a schematic diagram illustrating spectra Cb1 and Cg1 of combined sensitivity characteristics of a B-pixel CCD 103b and a G-pixel CCD 103g obtained when the LED 107d, which is the NU light source, and the LED 107b, which is the Y light source, are driven. In FIG. 7, as a reference, the emission spectra Ec, Ey, and Eni of the LEDs 107a to 107d illustrated in FIG. 4 are also illustrated.

As illustrated in FIG. 6, the CCD array 103A is configured such that pixels 103e are arranged in a two-dimensional matrix. Each of the pixels 103e includes an R-pixel CCD 103r that receives light of a red (R) component and accumulates an electric charge according to that light level; a G-pixel CCD 103g that receives light of a green (G) component and accumulates an electric charge according to that light level; and the B-pixel CCD 103b that receives light of a blue (B) component and accumulates an electric charge according to that light level.

As illustrated in FIG. 7, the wavelength (or the center wavelength) indicating the peak of the spectrum Sr of the spectral sensitivity characteristic of the R-pixel CCD 103r is located between the wavelengths (or the center wavelength) indicating the intensity peaks of emission spectra Ey and Eni of the Y light source (LED 107b) and the NI light source (LED 107c), respectively. In other words, the wavelengths have a distribution shape in which the peak wavelength of the spectral sensitivity characteristic of the R-pixel CCD 103r is located between the intensity peaks of the emission spectra Ey and Eni of the yellow (Y) and the near infrared light (NI) whose complementary color is red (R). Accordingly, as illustrated in FIG. 8, the sensitivity characteristic of the CCD 103r obtained when all of the light sources (LEDs 107a to 107d) emit light, i.e., the spectrum Cr of the sensitivity characteristic of the CCD 103r that is obtained by combining the spectrum Sr of the spectral sensitivity characteristic of the CCD 103r and the emission spectra Ec, Ey, Eni, and Enu of the LEDs 107a to 107d (hereinafter, referred to as an "R-pixel combined sensitivity characteristic"), has a substantially trapezoidal distribution shape with the center wavelength (for example, the wavelength associated with the peak wavelength of the spectrum Sr) being substantially flat and the attenuation from both shoulders of the spectrum Cr being sharper than that of the spectrum Sr.

Similarly, as illustrated in FIG. 7, the wavelength (or the center wavelength) indicating the peak of the spectrum Sg of the spectral sensitivity characteristic of the G-pixel CCD 103g is located between the wavelength (or the center wavelength) indicating the intensity peaks of emission spectra Ec and Ey of the C light source (LED 107a) and the Y light source (LED 107b). In other words, the wavelengths have a distribution shape in which the peak wavelength of the spectral sensitivity characteristic of the G-pixel CCD 103g is located between the intensity peaks of the emission spectra Ec and Ey of the cyan (C) and yellow (Y) whose complementary color is green (G). Accordingly, as illustrated in FIG. 8, the sensitivity characteristic of the CCD 103g obtained when all of the light sources (LED 107a to 107d) emit light, i.e., the spectrum Cg of the sensitivity characteristic of the CCD 103g that is obtained by combining the spectrum Sg of the spectral sensitivity characteristic of the CCD 103g and the emission spectra Ec, Ey, Eni, and Enu of the LEDs 107a to 107d (hereinafter, referred to as a "G-pixel combined sensitivity characteristic"), has a substantially trapezoidal distribution shape with the center wavelength (for example, the wavelength associated with the peak wavelength of the spectrum Sg) being substantially flat and attenuation from both shoulders of the spectrum Cg being sharper than that of the spectrum Sg.

Furthermore, as illustrated in FIG. 7, the wavelength (or the center wavelength) indicating the peak of the spectrum Sb of the spectral sensitivity characteristic of the B-pixel CCD 103b is shorter than that of the emission spectrum Ec of the C light source (LED 107a), i.e., the wavelength is located on the ultraviolet light side. Accordingly, as illustrated in FIG. 8, the sensitivity characteristic of the CCD 103b that is obtained when all of the light sources (LEDs 107a to 107d) emit light, i.e., the spectrum Cb of the sensitivity characteristic of the CCD 103b obtained by combining the spectrum Sb of the spectral sensitivity characteristic of the CCD 103b and the emission spectra Ec, Ey, Eni, and Enu of the LEDs 107a to 107d (hereinafter, referred to as a "G-pixel combined sensitivity characteristic), has a substantially trapezoidal distribution shape with the center wavelength (for example, the wavelength associated with the peak wavelength of the spectrum Sb) toward the infrared light side being substantially flat and attenuation from a shoulder of the spectrum Cb on the infrared light side being sharper than that of the spectrum Sb.

As described above, as illustrated in FIG. 8, in the first embodiment of the present invention, a portion near the peak of the combined sensitivity characteristic (spectrum Cb) obtained from both the emission spectrum Ec (Enu) of the LED 107a (LED 107d can also be included) and the spectral sensitivity characteristic (spectrum Sb) of the CCD 103b has a broad sensitivity characteristic. Similarly, a portion near the peak of the combined sensitivity characteristic (spectrum Cg, (or the spectrum Cr)) obtained from both the emission spectra Ec and Ey (or the emission spectra Ey and Eni) of the LEDs 107a and 107b (or the LEDs 107b and 107c) and spectral sensitivity characteristic (the spectrum Sg (or the spectrum Sr)) of the CCD 107g (or the LED 107r) also has a broad sensitivity characteristic. The broad sensitivity characteristic mentioned here means that, when compared with the spectral shape of the spectral sensitivity characteristic of each CCD or when compared with the spectral shape of the emission spectrum of each LED, the spectral shape is sufficiently flat to an extent that the wavelength dependency of the characteristic can be ignored or can be allowed as an error.

The height difference between the peak of the combined sensitivity characteristic (spectrum Cb) of a superimposed sensitivity characteristic (a first superimposed sensitivity characteristic), which is obtained by superimposing the combined sensitivity characteristic (on the long wavelength side of the spectrum Cb) of the CCD 103b with respect to the cyan (C) light on the combined sensitivity characteristic (spectrum Cg (or the spectrum Cr)) of the CCD 103g (or the CCD 103r) with respect to the combined light of the cyan (C) light (or the yellow (Y) light) and the yellow (Y) light (or the near infrared light (NI)), and the peak of the combined sensitivity characteristic (spectrum Cg (or the spectrum Cr)) is greater than the height difference between the peak of the combined sensitivity characteristic (on the short wavelength side of the spectrum Cb) of a superimposed sensitivity characteristic (a second superimposed sensitivity characteristic), which is obtained by superimposing the combined sensitivity characteristic (on the short wavelength side of the spectrum Cb) of the CCD 103*d* with respect to the near ultraviolet light (NU) on the combined sensitivity characteristic (on the long wavelength side of the spectrum Cb), and the peak of the combined sensitivity characteristic (on the long wavelength side of the spectrum Cb).

In the first embodiment of the present invention, cases are described as examples in which the peak wavelength (or the center wavelength) of the spectrum Sb is longer than the wavelength (or the center wavelength) indicating the intensity peak of the emission spectrum Enu of the NU light source (LED 107*d*); in which the wavelength band of the emission spectrum Enu is sufficiently narrower than the other emission spectra (Ec, Ey, and Eni); and in which the peak wavelength (or the center wavelength) of the emission spectrum Enu is sufficiently separated from the wavelength (or the center wavelength) indicating the intensity peak of the spectrum Sb of the receiving sensitivity characteristic of the CCD 103*b*. For example, a case is described in which a wavelength difference between the peak wavelength (or the center wavelength) of the emission spectrum Enu and the wavelength (or the center wavelength) indicating the intensity peak of the spectrum Sb of the receiving sensitivity characteristic of the CCD 103*b* is greater than a wavelength difference between the peak wavelength (or the center wavelength) of the emission spectrum Ec and the wavelength (or the center wavelength) indicating the intensity peak of the spectrum Sb of the receiving sensitivity characteristic of the CCD 103*b*. With this configuration, as described above, a depression (dropping part) of the light intensity is obtained between the light intensity distribution of the wavelength band that is mainly constituted by the special light from the LED 107*d* and the light intensity distribution of the wavelength band mainly constituted by the combined light emitted from the LEDs 107*a* to 107*c*. By doing so, the spectrum of the special light from the LED 107*d* is practically separated from the spectrum of the combined light constituted by light emitted from the LEDs 107*a* to 107*c*.

Accordingly, as illustrated in FIG. 8, for the sensitivity characteristic of the CCD 103*b* obtained when all of the light sources (LEDs 107*a* to 107*d*) emit light, i.e., for the spectrum Cb of the B-pixel combined sensitivity characteristic obtained by combining the spectrum Sb of the spectral sensitivity characteristic of the CCD 103*b* and the emission spectra Ec, Ey, Eni and Enu of the LEDs 107*a* to 107*d*, in the band from substantially center wavelength (for example, the wavelength associated with the peak wavelength of the spectrum Sb) toward the ultraviolet light side, a temporary drop in the sensitivity characteristic is formed between a portion near the peak wavelength of the emission spectrum Ec of the LED 107*a* and a portion near the peak wavelength of the emission spectrum Enu of the LED 107*d*. Accordingly, it is possible to separate the spectral sensitivity characteristic of the imaging unit 103 with respect to the special light emitted from the LED 107*d* from the spectral sensitivity characteristic of the imaging unit 103 with respect to the combined light constituted by light emitted from the other light sources (LEDs 107*a* to 107*c*). As a result, it is possible to make a special-light image, which is obtained using the special light as illumination light, clearer. It is preferable that the spectrum Cb have a distribution shape in which, on the ultraviolet light side of the spectrum Cb of the B-pixel combined sensitivity characteristic, attenuation from a shoulder of the spectrum Cb is also sharper than that of the spectrum Sb.

Furthermore, the sensitivity characteristic of the CCD 103*b* with respect to the near ultraviolet light (NU) from the LED 107*d* (hereinafter, referred to as a "first special light combined sensitivity characteristic") has a distribution shape that is obtained by combining, as illustrated in FIG. 9 using a spectrum Cb1, the emission spectrum Enu of the LED 107*d* and the spectrum Sb of the spectral sensitivity characteristic of the CCD 103*b*. Similarly, the sensitivity characteristic of the CCD 103*g* with respect to the yellow (Y) light from the LED 107*b* (hereinafter, referred to as a "second special light combined sensitivity characteristic) has a distribution shape that is obtained by combining, as illustrated in FIG. 9 using a spectrum Cg1, the emission spectrum Ey of the LED 107*b* and the spectrum Sg of the spectral sensitivity characteristic of the CCD 103*g*.

Accordingly, in the first embodiment of the present invention, by driving both the B-pixel CCD 103*b* and the G-pixel CCD 103*g* in the CCD array 103A while driving both the LED 107*d* and the LED 107*b* that emits the light of the emission spectrum Ey that is sufficiently separated from the emission spectrum Enu of the LED 107*d*, a special-light image made up of two special light components is acquired. Of the two special light, one is the near ultraviolet light (for example, light with a wavelength of about 415 nm: hereinafter, referred to as a "first special light") that is photoelectrically converted in accordance with the first special light combined sensitivity characteristic, whereas the other one is green light (for example, light with a wavelength of about 540 nm: hereinafter, referred to as a "second special light") that is photoelectrically converted in accordance with the second special light combined sensitivity characteristic.

Here, the transmittance of light inside the subject 900 varies in accordance with a wavelength. In other words, as the wavelength of light becomes shorter, the light reflects in the deeper portion in an inner wall of the subject 900. Furthermore, light with a wavelength of about 415 nm and light with a wavelength of about 540 nm tend to be absorbed by, for example, blood cells. Accordingly, by capturing an image inside the subject 900 using the first special light and the second special light, it is possible to acquire a special-light image in which the shapes of blood vessels in different depths are captured.

Furthermore, the complementary color of the cyan (C) and the near ultraviolet light (NU) can be light having a wavelength band that can be received by the B-pixel CCD 103*b*, i.e., can be blue (B). Instead of the CCD array 103A, various image-capturing devices, such as a complementary metal oxide semiconductor (CMOS) sensor array, can be used. Furthermore, instead of the LEDs 107*a* to 107*d*, various light-emitting elements can be used.

A description will be given by referring back to FIG. 3. The capsule control circuit 101 includes a memory that stores therein a program and a parameter for executing various operations. By appropriately reading the program and the parameter from the memory and executing them, the capsule control circuit 101 controls each unit arranged in the capsule endoscope 10. For example, by executing the read program in accordance with the read parameter, the capsule control circuit 101 allows the LED driving circuit 106 in the illumination unit 107 to emit any combination of light from the LEDs 107*a* to 107*d*. The capsule control circuit 101 also allows the imaging unit 103 to periodically create, one after the other, an image signal of a normal-light image and an image signal of a special-light image. Furthermore, after the capsule control circuit 101 allows the image signal processing circuit 104 to perform a process on the image signal obtained by the imaging unit 103, the capsule control circuit 101 allows the wireless transmitting/receiving circuit 105 to wirelessly transmit the processed image signal.

The image signal processing circuit 104 performs, for example, a signal process, such as analog to digital (A/D) conversion, on a received image signal. The wireless transmitting/receiving circuit 105 converts the received and processed image signal to a signal for wireless transmission and sends it as a wireless signal to the transmitting antenna 105*t*. It is also possible to configure such that the wireless transmitting/receiving circuit 105 receives, from the receiving device 20, which will be described later, a control signal that is wirelessly transmitted via the receiving antenna 105*r* and inputs it to the capsule control circuit 101, and the capsule control circuit 101 performs various operations in accordance with the received control signal.

The battery 108 and the power circuit 109 supply electrical power to each unit in the capsule endoscope 10. Examples of the battery 108 include a primary battery or a secondary battery, such as a button battery.

Receiving Device

Figure 10:
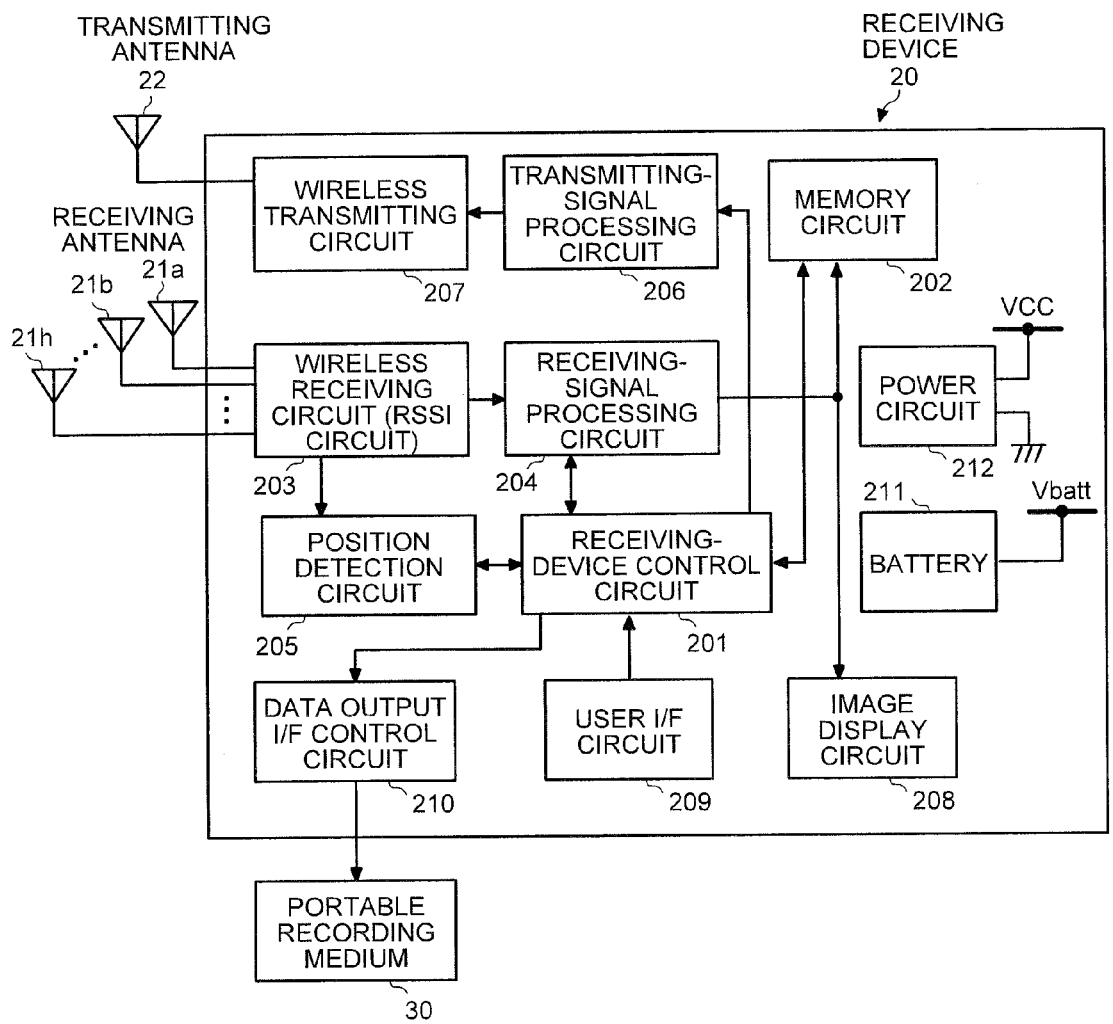
FIG. 10 is a block diagram illustrating, in outline, the configuration of a receiving device according to the first embodiment of the present invention.

In the following, the configuration of the receiving device 20 according to the first embodiment of the present invention will be described in detail with reference to the drawings. FIG. 10 is a block diagram illustrating, in outline, the configuration of the receiving device 20 according to the first embodiment of the present invention.

As illustrated in FIG. 10, the receiving device 20 includes a wireless receiving circuit 203 to which the receiving antenna 21 that is attached on the surface of the subject 900 is connected; a receiving-signal processing circuit 204 that performs a predetermined process on a receiving signal that is received via the receiving antenna 21 and the wireless receiving circuit 203; a position detection circuit 205 that detects the position of the capsule endoscope 10 inside the subject 900 using radio field intensity of the receiving signal detected at a received signal strength indication (RSSI) circuit in the wireless receiving circuit 203; a transmitting-signal processing circuit 206 that performs a predetermined process on, for example, a control signal that is sent to the capsule endoscope 10; a wireless transmitting circuit 207 that wirelessly transmits, via the transmitting antenna 22, a transmitting signal that is processed in the transmitting-signal processing circuit 206; a receiving-device control circuit 201 that controls each circuit in the receiving device 20; a memory circuit 202 that stores therein a program and a parameter executed by the receiving-device control circuit 201 for controlling each circuit and that stores therein, for example, image data of an image received from the capsule endoscope 10; an image display circuit 208 that displays, to a user, an image received from the capsule endoscope 10 or various setting screens with respect to the receiving device 20; a user I/F circuit 209 that is used by a user to instruct various settings to the receiving device 20 or the capsule endoscope 10; a data output I/F control circuit 210 that outputs, for example, image data of an image received from the capsule endoscope 10 to the detachable portable recording medium 30; and a battery 211 and a power circuit 212, which supply electrical power to each circuit in the receiving device 20.

In the receiving device 20, the wireless receiving circuit 203 receives an image signal that is periodically sent via the receiving antenna 21 and inputs the received image signal to the receiving-signal processing circuit 204. The receiving-signal processing circuit 204 performs a predetermined process on the received image signal, creates image data, and inputs the created image data to the memory circuit 202 and the image display circuit 208. The image data that is input to the memory circuit 202 is temporarily stored in the memory circuit 202. By replaying the input image data, the image display circuit 208 displays, to a user, an image sent from the capsule endoscope 10.

The wireless receiving circuit 203 in the receiving device 20 inputs, to the position detection circuit 205, the radio field intensity of the receiving signal at each receiving antenna 21 that is detected by the RSSI circuit. Under the control of the receiving-device control circuit 201, the position detection circuit 205 detects the position of the capsule endoscope 10 inside the subject 900 in accordance with the position of each receiving antenna 21 on the surface of the subject 900 and in accordance with the radio field intensity of the receiving signal received by each receiving antenna 21, using, for example, three-dimensional positioning. Furthermore, the position detection circuit 205 inputs, via the receiving-device control circuit 201, position information on the detected capsule endoscope 10 to the receiving-signal processing circuit 204 or the memory circuit 202. For example, if the position information is input to the receiving-signal processing circuit 204, the receiving-signal processing circuit 204 adds image data corresponding to the receiving signal that is used for position detection to the position information and inputs, to the memory circuit 202, the image data to which the position information is added. In contrast, if the position information is input to the memory circuit 202, the receiving signal control circuit 201 controls the memory circuit 202 in such a manner that new position information is added to the image data that is stored, in the immediately before process, in the memory circuit 202.

The image data to which the position information is added is read from the memory circuit 202 by the receiving-device control circuit 201 and is then input to the portable recording medium 30 via the data output I/F control circuit 210. Accordingly, the image data to which the position information is added is stored in the portable recording medium 30.

Display Device

Figure 11:
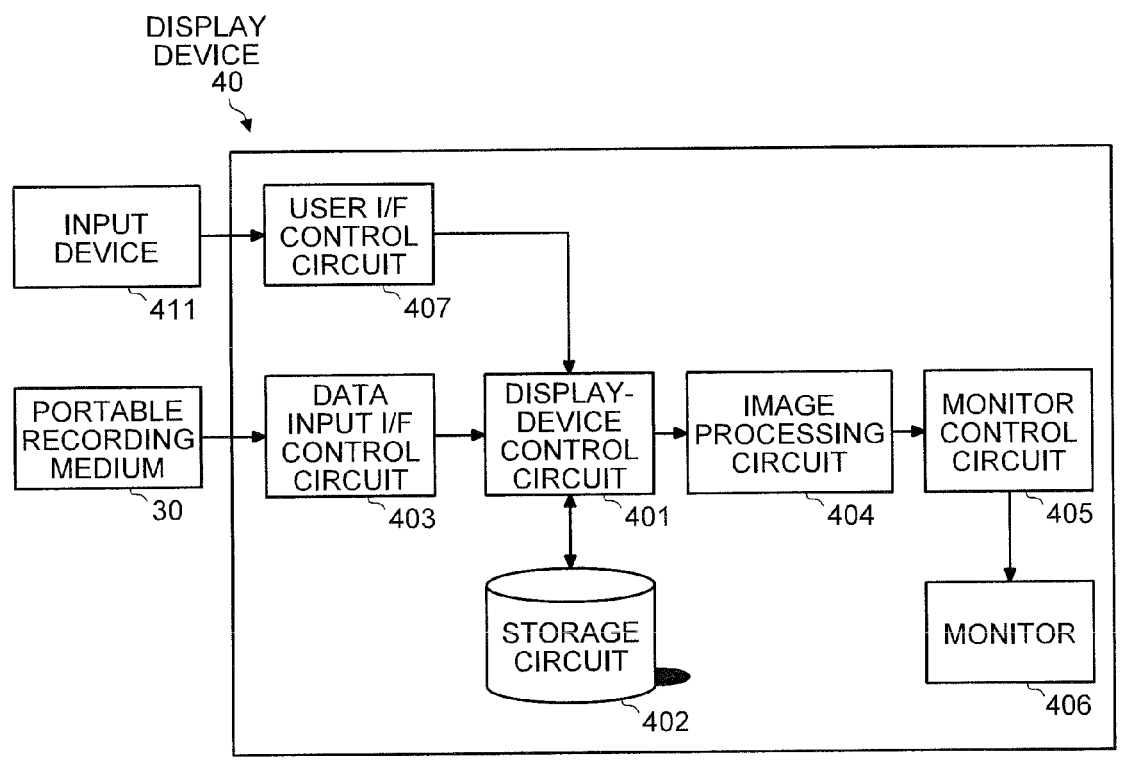
FIG. 11 is a block diagram illustrating, in outline, the configuration of a display device according to the first embodiment of the present invention.

In the following, the configuration of the display device 40 according to the first embodiment of the present invention will be described in detail with reference to the drawings. FIG. 11 is a block diagram illustrating, in outline, the configuration of the display device 40 according to the first embodiment of the present invention.

As illustrated in FIG. 11, the display device 40 includes a display-device control circuit 401 that controls each circuit in the display device 40; a storage circuit 402 that stores therein various programs and parameters performed by the display-device control circuit 401 and that stores therein image data or the like received from the receiving device 20; a data input I/F control circuit 403 that inputs the image data that is received and stored in the portable recording medium 30; a user I/F control circuit 407 that is an interface with respect to an input device 411 that is used for an operation input from a user who uses a mouse, a keyboard, a joystick, or the like; an image processing circuit 404 that creates, using the image data that is input via the display-device control circuit 401, various graphical user interface (GUI) screens that allow a user to observe an image obtained by the capsule endoscope 10; a monitor control circuit 405 that displays, on a monitor 406, the GUI screens created by the image processing circuit 404; and the monitor 406 constituted by a liquid crystal display, an organic/inorganic electro-luminescence (EL) display, or the like.

If a user stores, in the portable recording medium 30 using the receiving device 20, image data sent from the capsule endoscope 10, the user removes the portable recording medium 30 from the receiving device 20 and inserts it to the display device 40. Then, by inputting various instructions to the display device 40 using the input device 411 connected to the display device 40, the user displays, on the monitor 406, the GUI screen of the image that is stored in the portable recording medium 30 and inputs, while observing inside the subject 900 using the GUI screen, various operation instructions with respect to the display device 40 as needed.

Operation

Figure 12:
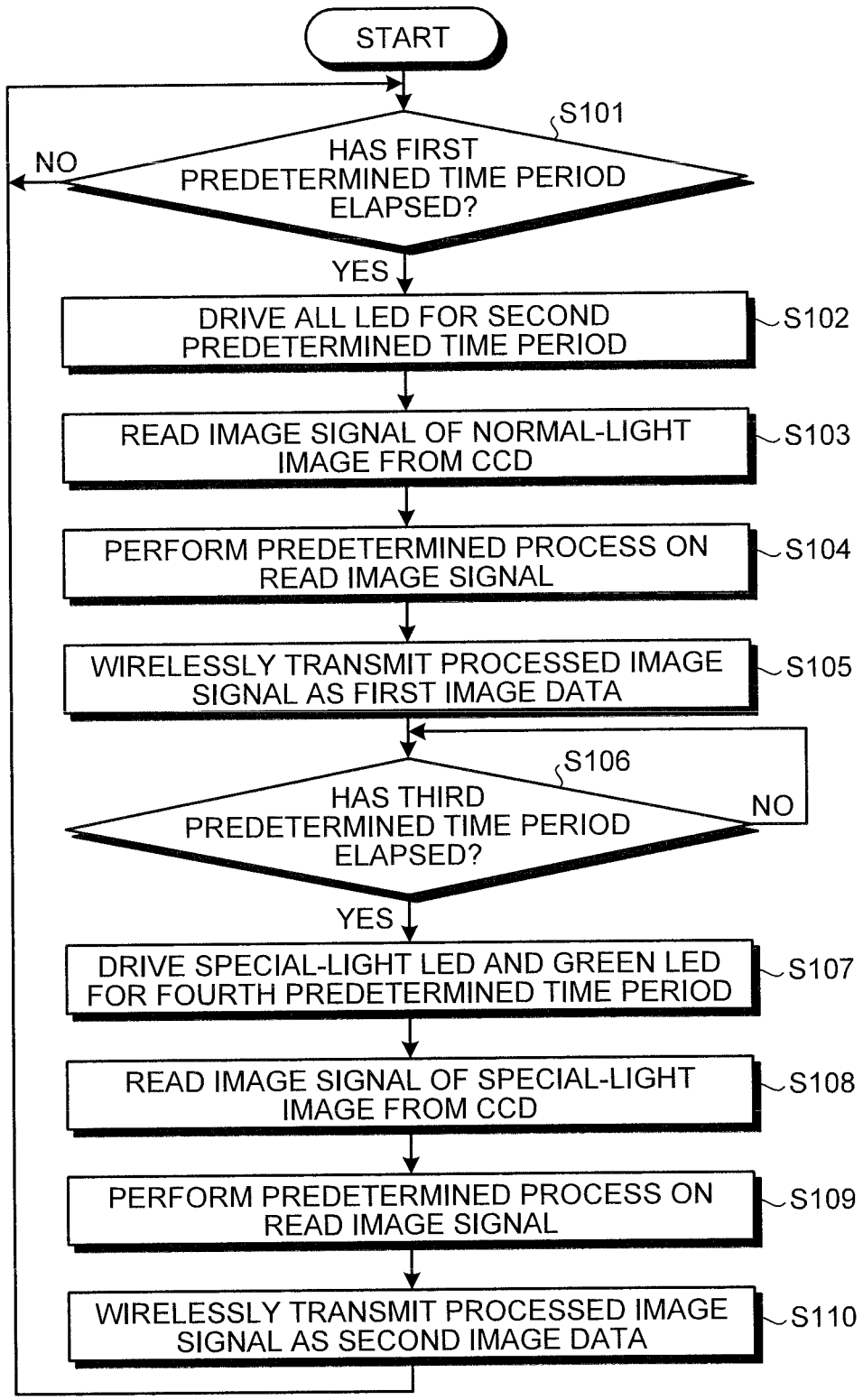
FIG. 12 is a flowchart illustrating, in outline, an example flow performed by the capsule endoscope according to the first embodiment of the present invention.

In the following, the operation of the capsule endoscope system 1 according to the first embodiment of the present invention will be described in detail. First, the operation of the capsule endoscope 10 according to the first embodiment of the present invention will be described. FIG. 12 is a flowchart illustrating, in outline, an example flow performed by the capsule endoscope 10 according to the first embodiment of the present invention. In FIG. 12, a description will be given by focusing on the operation of the capsule control circuit 101 that controls each circuit in the capsule endoscope 10.

As illustrated in FIG. 12, the capsule control circuit 101 determines whether a first predetermined time period has elapsed after it is started (Step S101). If the first predetermined time period has elapsed (Yes at Step S101), first, by controlling the LED driving circuit 106, the capsule control circuit 101 allows all of the LEDs 107a to 107d to emit light for a second predetermined time period (Step S102). Subsequently, by driving the CCD driving circuit 102, the capsule control circuit 101 reads the electric charges accumulated in all of the CCDs 103r, 103g, and 103b in the CCD array 103A (Step S103); inputs, to the image signal processing circuit 104, an image signal of a normal-light image that is obtained by the reading process; and performs, in the image signal processing circuit 104, a predetermined process on the image signal (Step S104). The processed image signal is input to the wireless transmitting/receiving circuit 105. Thereafter, by controlling the wireless transmitting/receiving circuit 105, the capsule control circuit 101 wirelessly transmits, to the receiving device 20, the image signal of the normal-light image as first image data (Step S105). If the first predetermined time period has not elapsed (No at Step S101), the capsule control circuit 101, for example, waits. A time, for example, of capturing an image or of performing a signal process can also be added, as a time stamp, to the first image data that is wirelessly transmitted to the receiving device 20. From Steps S101 to S105, a first image capturing mode is operated, where a normal-light image is obtained.

Then, the capsule control circuit 101 determines whether a third predetermined time period has elapsed after a process at Step S101 is performed (Step S106). If the third predetermined time period has elapsed (Yes at Step S106), first, by controlling the LED driving circuit 106, the capsule control circuit 101 allows both the LED 107d that is the near ultraviolet light (NU) light source and the LED 107b that is the Y light source to emit light for a fourth predetermined time period (Step S107). Subsequently, by driving the CCD driving circuit 102, the capsule control circuit 101 reads the electric charge accumulated in the CCDs 103b and 103g in the CCD array 103A (Step S108); inputs, to the image signal processing circuit 104, an image signal of a special-light image obtained by the reading process; and performs, in the image signal processing circuit 104, a predetermined process on the image signal (Step S109). The processed image signal is input to the wireless transmitting/receiving circuit 105. Thereafter, by controlling the wireless transmitting/receiving circuit 105, the capsule control circuit 101 wirelessly transmits, to the receiving device 20, the image signal of the special-light image as second image data (Step S110). If the second predetermined time period has not elapsed (No at Step S106), the capsule control circuit 101, for example, waits. A time, for example, of capturing an image or of performing a signal process can be added, as a time stamp, to the second image data that is wirelessly transmitted to the receiving device 20. From Steps S106 to S110, a second image capturing mode is operated, where a special-light image is obtained.

In this way, the first image data of the normal-light image and the second image data of the special-light image are periodically sent, one after the other, from the capsule endoscope 10 to the receiving device 20. The receiving device 20 adds position information on the capsule endoscope 10 at the time of image capturing to the received first and second image data; performs the predetermined process in the receiving-signal processing circuit 204; and then inputs the first and the second image data to the portable recording medium 30 via the data output I/F control circuit 210. The display device 40 to which the first and the second image data is input via the portable recording medium 30 creates, in accordance with, for example, an instruction from a user, a GUI screen using the received first and/or second image data and displays this GUI screen on the monitor 406, whereby providing the user with an observation environment inside the subject 900.

With the configuration and operation described above, in the first embodiment of the present invention, in addition to the light sources (LEDs 107a to 107c (LED 107d can also be included) that are used to obtain the normal-light image (the first image), the light source (LED 107d) that is used to obtain the special-light image (the second image) is additionally arranged. By driving these light sources in combination, the normal-light image and the special-light image are obtained. Accordingly, it is possible to provide the capsule endoscope system 1 and the capsule endoscope 10 capable of obtaining the normal-light image and the special-light image without increasing the burden imposed on the image processing.

Furthermore, in the first embodiment of the present invention, the normal-light image and the special-light image are periodically obtained by changing the combination of the light sources (LEDs 107a to 107d) that are automatically driven in the capsule endoscope 10; however, the present invention is not limited thereto. For example, the combination of the light sources (LEDs 107a to 107d) to be driven can also be selected by operating the capsule endoscope 10 from the receiving device 20.

Modification 1-1

In the first embodiment described above, the CCD array 103A in which a single pixel 103e includes CCDs 103r, 103g, and 103b for the three primary colors (an R pixel, a G pixel, and a B pixel) is used as an example; however, the present invention is not limited thereto. In the following, as modification 1-1 of the first embodiment of the present invention, another type of CCD array 103A will be described in detail with reference to the drawings.

Figure 13:
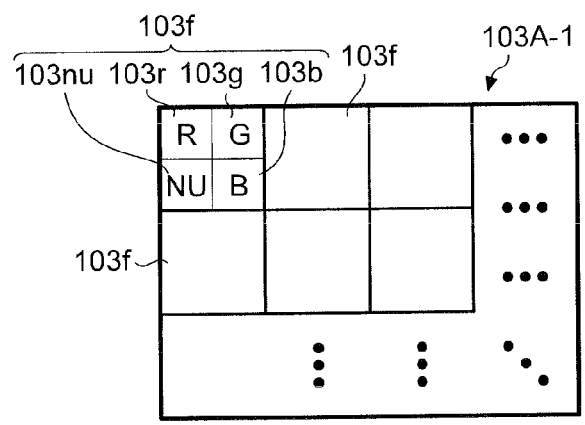
FIG. 13 is a schematic diagram illustrating an example configuration of a CCD array according to modification 1-1 of the first embodiment of the present invention.
Figure 14:
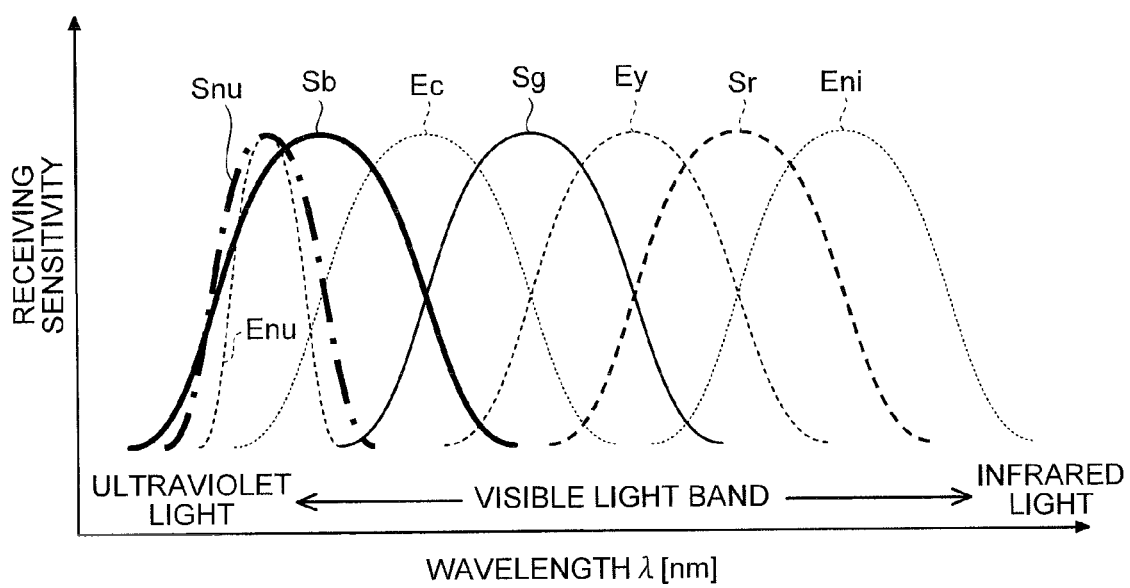
FIG. 14 is a schematic diagram illustrating spectra of spectral sensitivity characteristics of each CCD according to the modification 1-1 of the first embodiment of the present invention.

FIG. 13 is a schematic diagram illustrating an example configuration of a CCD array 103A-1 according to the modification 1-1 of the first embodiment of the present invention. FIG. 14 is a schematic diagram illustrating spectra Sr, Sg, Sb, and Snu of the spectral sensitivity characteristics of each of the CCDs 103r, 103g, 103b, and 103nu, respectively. In FIG. 14, the emission spectra Ec, Ey, and Eni of the LEDs 107a to 107d, which are illustrated in FIG. 4, are also illustrated as a reference.

In the first embodiment described above, a case is described, as an example, in which the first special light with a wavelength of about 415 nm and the second special light with a wavelength of about 540 nm are used as special light that is used when the special-light image is obtained. An image constituted by these color components is obtained as a special-light image (the second image data). In the modification 1-1, as illustrated in FIG. 13, a case is described, as an example, in which the CCD array 103A-1 is configured such that pixels 103f, each of which includes a near ultraviolet light (NU) pixel CCD 103nu in addition to the R-pixel CCD 103r, the G-pixel CCD 103g, and the B-pixel CCD 103b, are arranged in a two-dimensional matrix.

The CCDs 103r, 103g, and 103b in the modification 1-1 are the same as those in the first embodiment. However, as illustrated in FIG. 14, the CCD 103nu has a spectral sensitivity characteristic of the spectrum Snu whose wavelength (or the center wavelength) indicating the sensitivity peak thereof is substantially the same that of the emission spectrum Enu of the LED 107d that is the NU light source.

Specifically, in the modification 1-1, because each pixel 103f of the CCD array 103A-1 includes the CCD 103nu that emits, as illumination light, the near ultraviolet light (the first special light) from the LED 107d with a wavelength of about 415 nm, it is possible to obtain a clearer special-light image. Because the other configurations, operations, and advantages are the same as those described in the first embodiment, a description thereof in detail will be omitted here.

Modification 1-2

Figure 15:
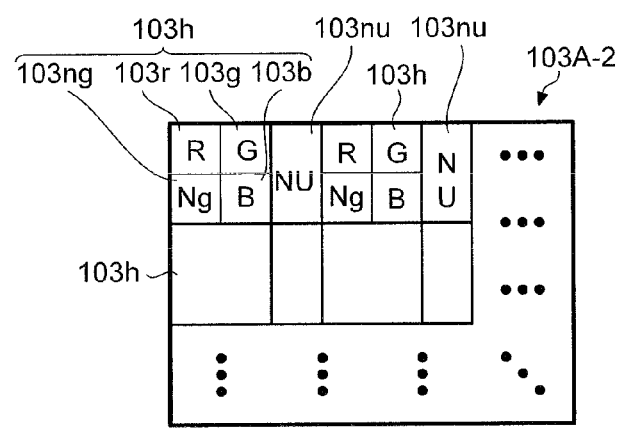
FIG. 15 is a schematic diagram illustrating an example configuration of a CCD array according to modification 1-2 of the first embodiment of the present invention.
Figure 16:
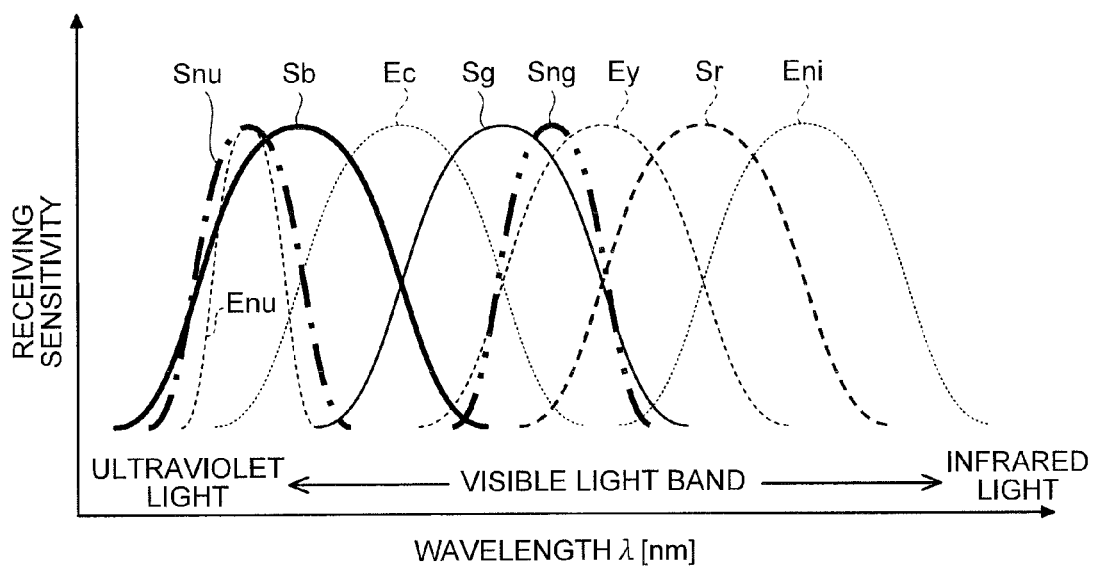
FIG. 16 is a schematic diagram illustrating spectra of spectral sensitivity characteristics of each CCD according to the modification 1-2 of the first embodiment of the present invention.

Furthermore, as modification 1-2 of the first embodiment of the present invention, another type of CCD array 103A that has been described above will be described in detail with reference to the drawings. FIG. 15 is a schematic diagram illustrating an example configuration of a CCD array 103A-2 according to the modification 1-2. FIG. 16 is a schematic diagram illustrating spectra Sr, Sg, Sb, Snu, and Sng of the spectral sensitivity characteristics of each of the CCDs 103r, 103g, 103b, 103nu, and 103ng, respectively. In FIG. 16, the emission spectra Ec, Ey, and Eni of the LEDs 107a to 107d, which are illustrated in FIG. 4, are also illustrated as a reference.

In the modification 1-1 described above, a case is described as an example in which each pixel 103f includes the CCD 103nu that emits, as illumination light, the near ultraviolet light (the first special light) with a wavelength of about 415 nm. In the modification 1-2, in addition to the CCD 103nu, each pixel 103h further includes a CCD 103ng that emits, as illumination light, light (the second special light) with a wavelength of about 540 nm. Accordingly, as illustrated in FIG. 15, in addition to the R-pixel CCD 103r, the G-pixel CCD 103g, the B-pixel CCD 103b, and an NU-pixel CCD 103nu, the CCD array 103A-2 according to the modification 1-2 is configured such that, pixels 103h, each of which includes a pixel (NG-pixel) CCD 103ng that receives the second special light, are arranged in a two-dimensional matrix. The CCDs 103r, 103g, 103b, and 103nu in the modification 1-2 are the same as those in the modification 1-1 described above. However, as illustrated in FIG. 16, the spectrum Sng of the spectral sensitivity characteristic of the CCD 103ng has a distribution shape in which the wavelength (or the center wavelength) indicating the sensitivity peak thereof is about 540 nm.

As described above, because the CCDs 103nu and 103ng that emit, as illumination light, the first special light and the second special light, respectively, are included in a single pixel 103h, it is possible to obtain a further clearer special-light image. Because the other configurations, operations, and advantages are the same as those described in the first embodiment, a description thereof in detail will be omitted here.

Modification 1-3

In the first embodiment or in the modifications thereof, the capsule endoscope 10 sequentially sends, to the receiving device 20, the normal-light image (the first image data) and the special-light image (the second image data) after the capsule endoscope 10 obtained them. However, the present invention is not limited thereto. For example, it is also possible to configure such that one or more normal-light image (the first image data) and one or more special-light image (the second image data) can be sent to the receiving device 20 at a time. In the following, this case will be described in detail as modification 1-3 of the first embodiment with reference to the drawings. In the following description, elements that have the same configuration as in the first embodiment are assigned the same reference numerals, and a description thereof in detail is omitted.

Figure 17:
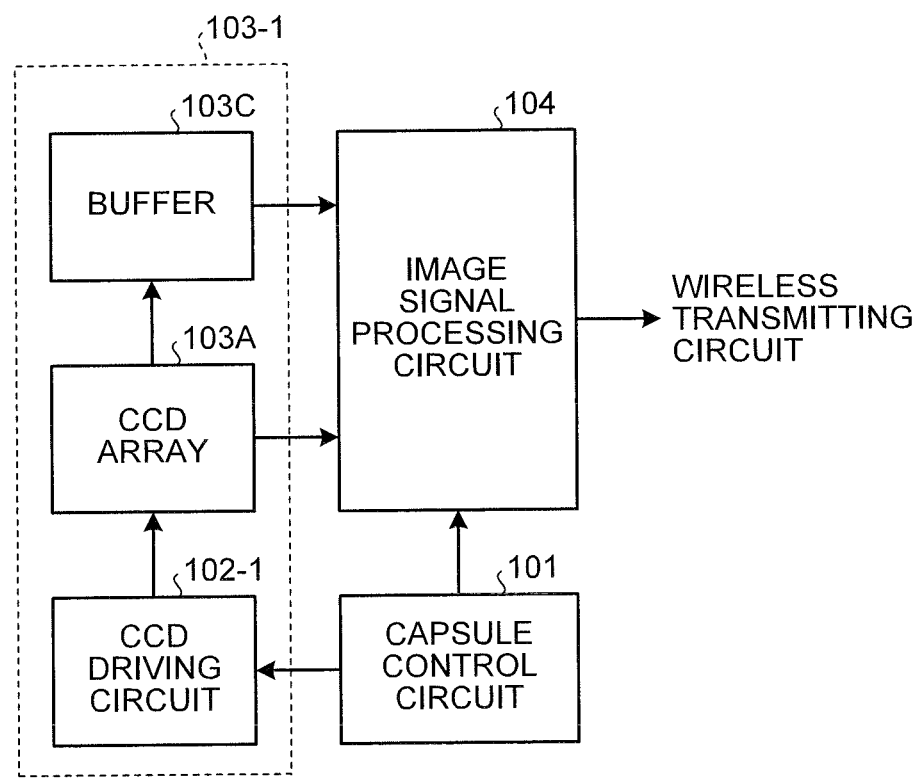
FIG. 17 is a block diagram illustrating, in outline, an example configuration of an imaging unit and peripheral circuits thereof according to modification 1-3 of the first embodiment of the present invention.

FIG. 17 is a block diagram illustrating, in outline, an example configuration of an imaging unit 103-1 and peripheral circuits thereof according to the modification 1-3 of the first embodiment of the present invention. As illustrated in FIG. 17, the imaging unit 103-1 according to the modification 1-3 includes the CCD array 103A, a CCD driving circuit 102-1, and a buffer 103C.

The buffer 103C is a page memory that temporarily stores therein an image signal that is created by the CCD array 103A. Under the control of the capsule control circuit 101, the CCD driving circuit 102-1 temporarily stores, in the buffer 103C, an image signal of the normal-light image created by the CCD array 103A and then allows the CCD array 103A to create an image signal of the special-light image. Furthermore, under the control of the capsule control circuit 101, the image signal processing circuit 104 reads, for example, the image signal of the normal-light image stored in the buffer 103C; performs a predetermined process on the image signal; outputs the processed image signal to the wireless transmitting/receiving circuit 105; subsequently reads, from the CCD array 103A, the image signal of the special-light image; performs a predetermined process on the image signal; and outputs the processed image signal to the wireless transmitting/receiving circuit 105. The wireless transmitting/receiving circuit 105 sends the received image signal of the normal-light image and the received image signal of the special-light image to the receiving device 20 in a single sending process.

Figure 18:
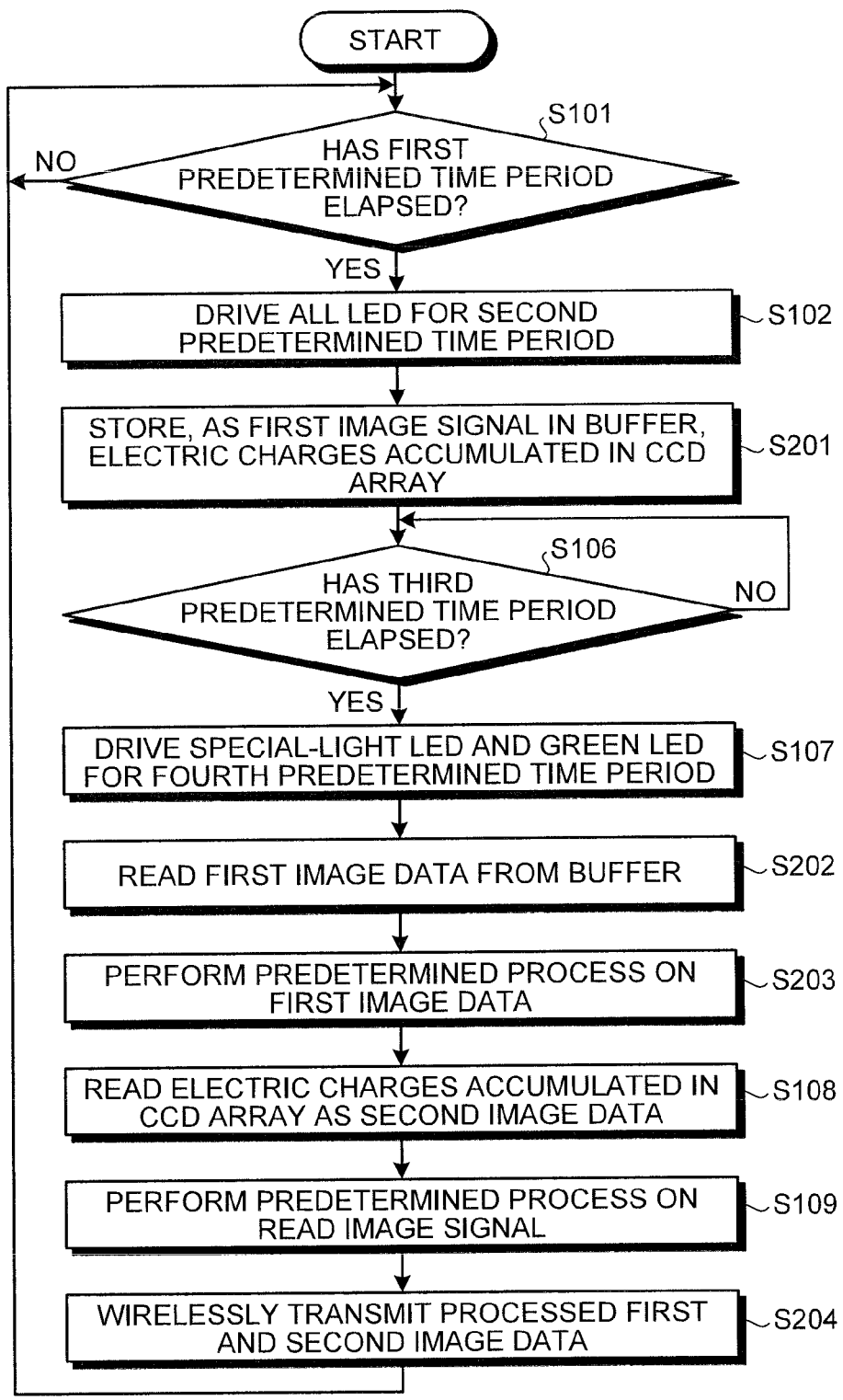
FIG. 18 is a flowchart illustrating, in outline, an example flow performed by a capsule control circuit according to the modification 1-3 of the first embodiment of the present invention.

In the following, the operation performed by the capsule control circuit 101 according to the modification 1-3 will be described in detail with reference to the drawings. FIG. 18 is a flowchart illustrating, in outline, an example flow performed by the capsule control circuit 101 according to the modification 1-3 of the first embodiment of the present invention.

As illustrated in FIG. 18, by performing the same operations as those at Steps S101 and S102 illustrated in FIG. 12, the capsule control circuit 101 allows all of the LEDs 107a to 107d to emit light for the second predetermined time period (Steps S101 and S102 in FIG. 18). Subsequently, by driving the CCD driving circuit 102-1, the capsule control circuit 101 stores, as first image data in the buffer 103C, electric charges accumulated in all of the CCDs 103r, 103g, and 103b in the CCD array 103A (Step S201). The matrix structure of the CCD array 103A and the matrix structure of the buffer 103C are preferably mirrored. With this structure, by moving an electric charge generated in the CCD array 103A to the buffer 103C without processing anything, it is possible to easily store the image signal created by the CCD array 103A in the buffer 103C.

Then, by performing the same operations as those at Steps S106 and S107 illustrated in FIG. 12, the capsule control circuit 101 allows the LED 107d that is the near ultraviolet light (NU) light source and the LED 107b that is the Y light source to emit light (Steps S106 and S107 in FIG. 18). Subsequently, the capsule control circuit 101 reads the first image data that is stored in the buffer 103C (Step S202) and inputs the first image data to the image signal processing circuit 104, where a predetermined process is performed on the image data (Step S203). The processed first image data is input to the wireless transmitting/receiving circuit 105.

Then, by performing the same operations as those at Steps S108 and S109 illustrated in FIG. 12, the capsule control circuit 101 reads, as the second image data, the electric charges accumulated in the CCD 103b and 103g in the CCD array 103A and performs a predetermined process on them (Steps S108 and S109 in FIG. 18). The processed second image data is input to the wireless transmitting/receiving circuit 105. Thereafter, by controlling the wireless transmitting/receiving circuit 105, the capsule control circuit 101 wirelessly transmits the first and second image data to the receiving device 20 in a single sending process (Step S204).

With the operation described above, because the first image data and the second image data can be sent to the receiving device 20 in a single sending process, it is possible to reduce the time and the burden imposed on the sending process. Because the other configurations, operations, and advantages are the same as those described in the first embodiment or the modifications thereof, a description thereof in detail will be omitted here.

Second Embodiment

In the following, an in-vivo observation system and a body-insertable apparatus according to a second embodiment of the present invention will be described in detail with reference to the drawings. In the following description, elements that have the same configuration as in the first embodiment or in the modifications thereof are assigned the same reference numerals, and a description thereof in detail is omitted.

Figure 19:
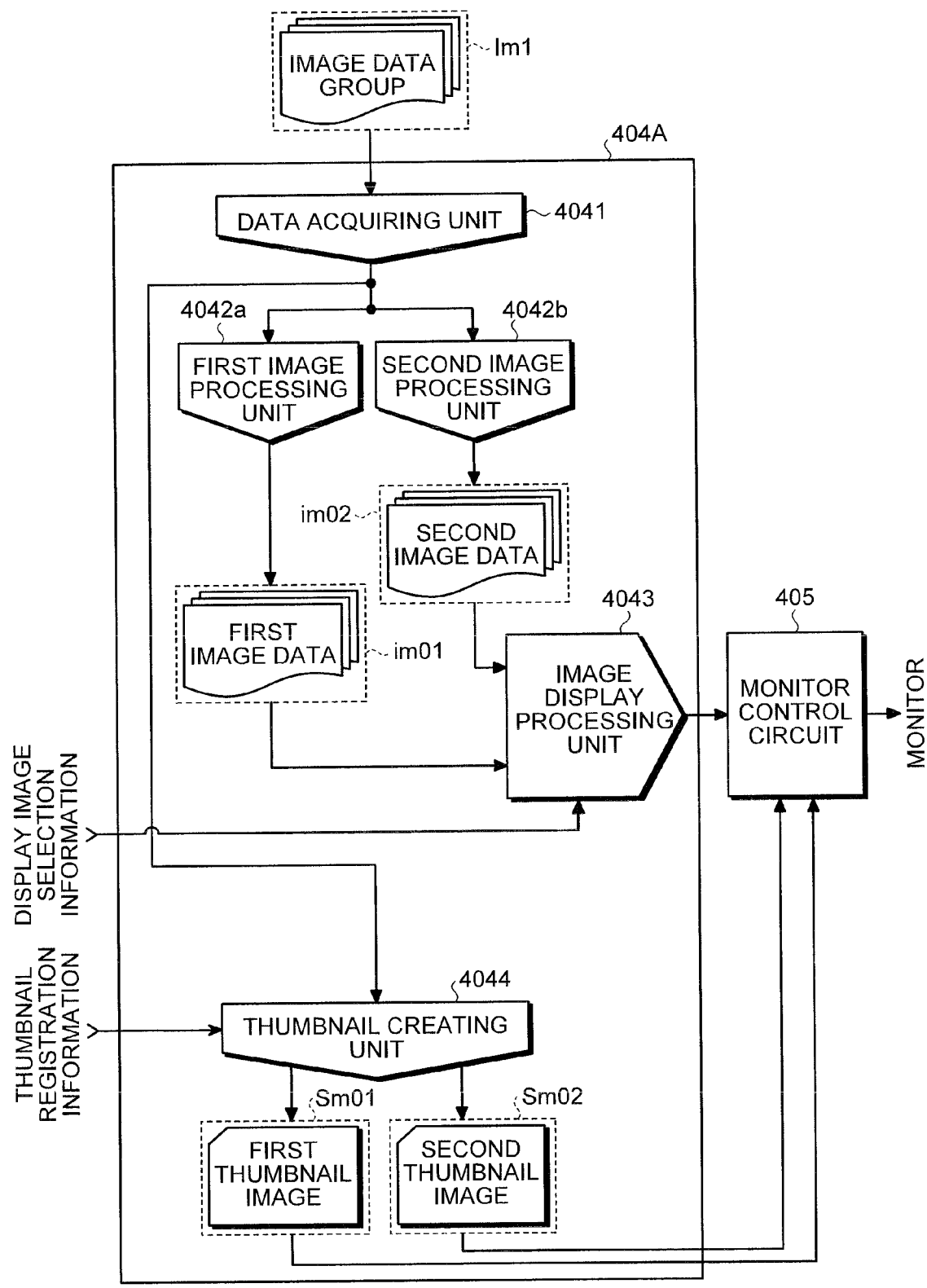
FIG. 19 is a block diagram illustrating, in outline, the configuration of an image processing circuit and a peripheral circuit thereof according to a second embodiment of the present invention.

In the second embodiment, it is possible to use a structure similar to the capsule endoscope system 1 according to the first embodiment. However, in the second embodiment, the image processing circuit 404 in the display device 40 illustrated in FIG. 11 is replaced by an image processing circuit 404A illustrated in FIG. 19. FIG. 19 is a block diagram illustrating, in outline, the configuration of the image processing circuit 404A and a peripheral circuit thereof according to a second embodiment of the present invention.

As illustrated in FIG. 19, the image processing circuit 404A includes a data acquiring unit 4041 that obtains, for example, from the storage circuit 402 via the display-device control circuit 401, at least one piece of image data (hereinafter, referred to as an "image data group im1"); a first image processing unit 4042a that performs a predetermined process on first image data in the image data group im1 obtained by the data acquiring unit 4041; a second image processing unit 4042b that performs a predetermined process on second image data in the image data group im1 obtained by the data acquiring unit 4041; an image display processing unit 4043 that selects, from processed first image data im01 and second image data im02 in accordance with an instruction (display image selection information) that is input from the input device 411 via the user I/F control circuit 407, an image to be displayed on the monitor 406 (see FIG. 11) and then creates a GUI screen using the selected first image data im01 or second image data im02; and a thumbnail creating unit 4044 that creates a thumbnail image, in accordance with the instruction (thumbnail registration information) that is input via the user I/F control circuit 407, from the first or the second image data that is to be displayed using thumbnail and that is in the image data group im1 obtained by the data acquiring unit 4041.

The GUI screen created by the image display processing unit 4043 is input to the monitor control circuit 405 and is displayed on the monitor 406 under the control of the monitor control circuit 405. A first thumbnail image Sm01 and a second thumbnail image Sm02 that are created by the thumbnail creating unit 4044 are input to the monitor control circuit 405. The monitor control circuit 405 appropriately embeds the received first and second thumbnail images Sm01 and Sm02 in the GUI screen (see thumbnail images Sm1 and Sm2 in FIGS. 22 to 25). The GUI screen in which the first and second thumbnail images Sm01 and Sm02 are embedded is input to the monitor 406. Accordingly, the GUI screens like those illustrated in FIGS. 20 to 25 are displayed on the monitor 406.

Figure 20:
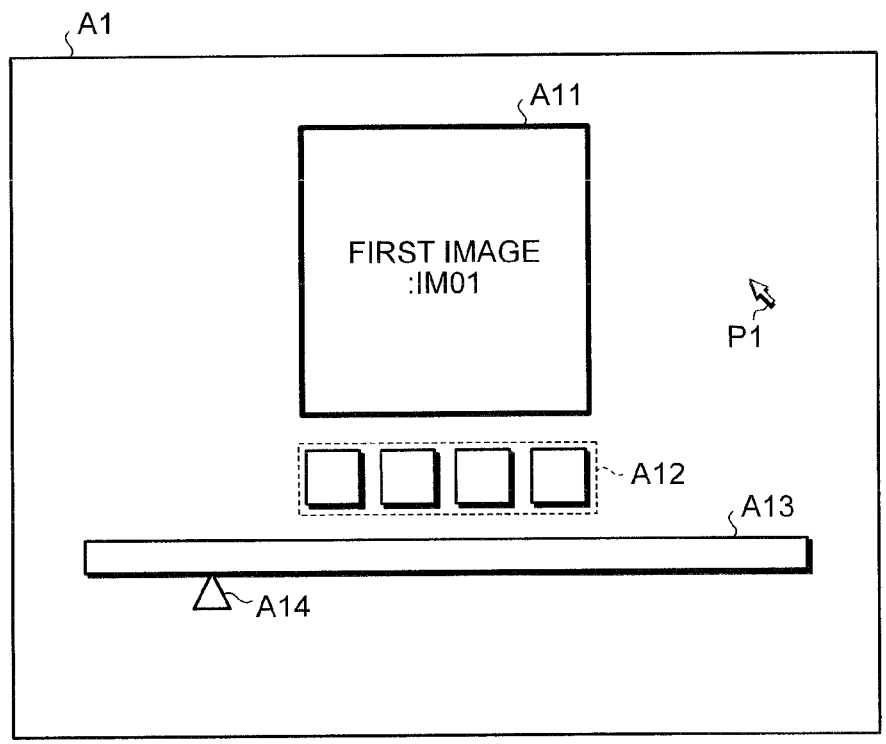
FIG. 20 are schematic diagrams illustrating examples, according to the second embodiment of the present invention, of a GUI screen displaying a first image, which is a normal-light image, and a GUI screen displaying a second image, which is a special-light image.
Figure 20:
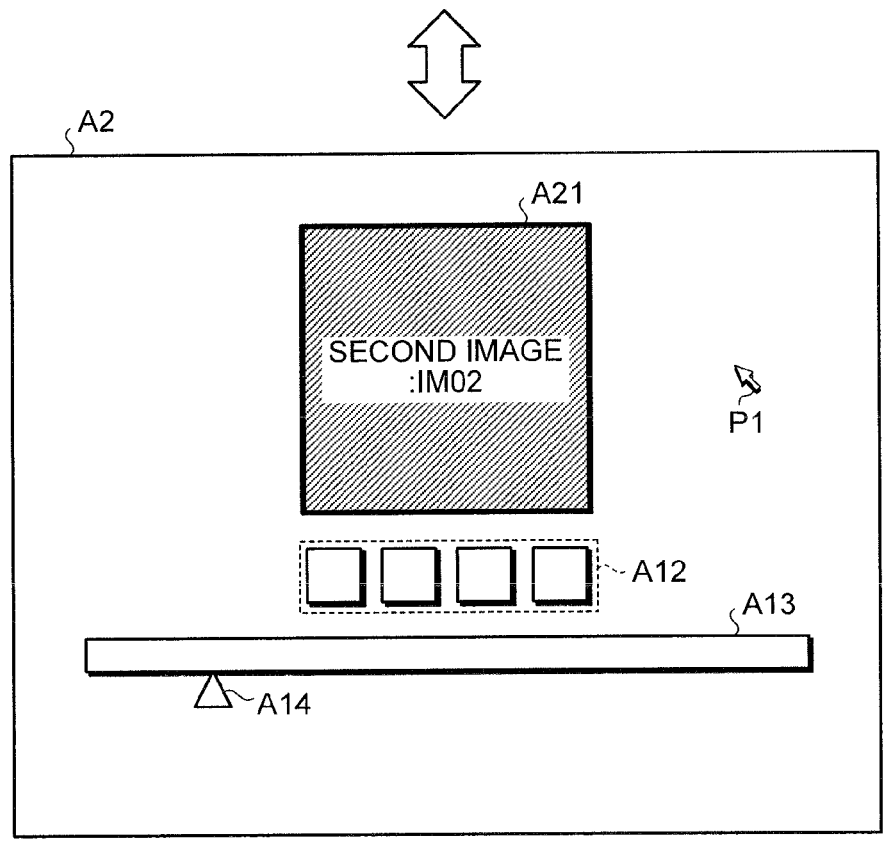
Figure 21:
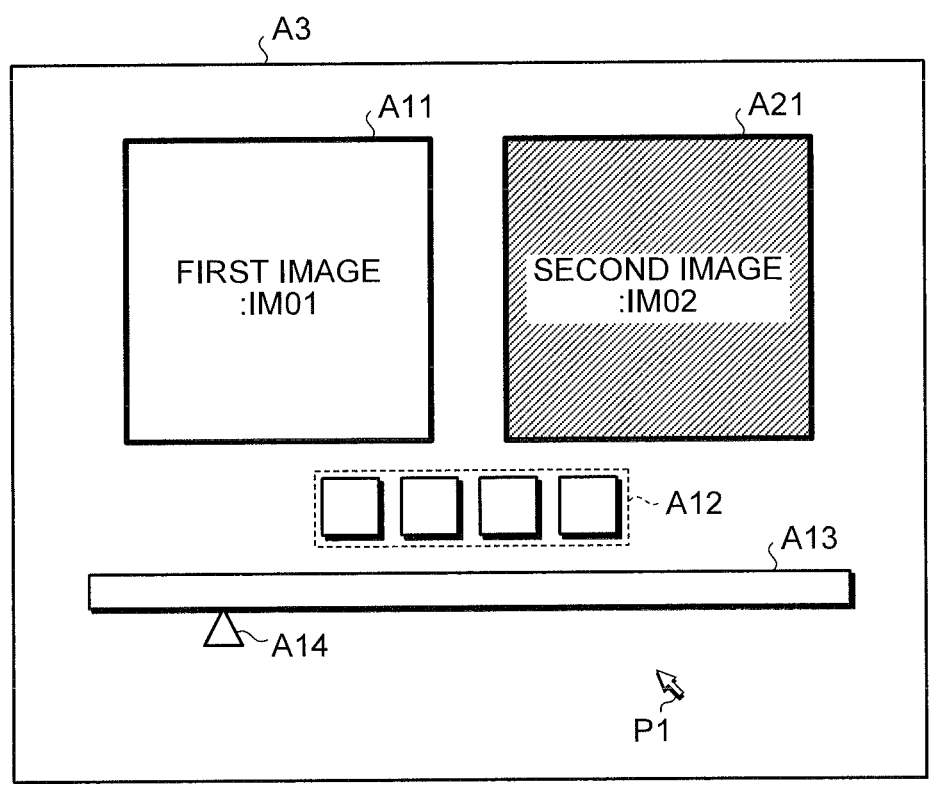
FIG. 21 is a schematic diagram illustrating an example, according to the second embodiment of the present invention, of a GUI screen that displays, in parallel, the first image and the second image according to the second embodiment of the present invention.
Figure 22:
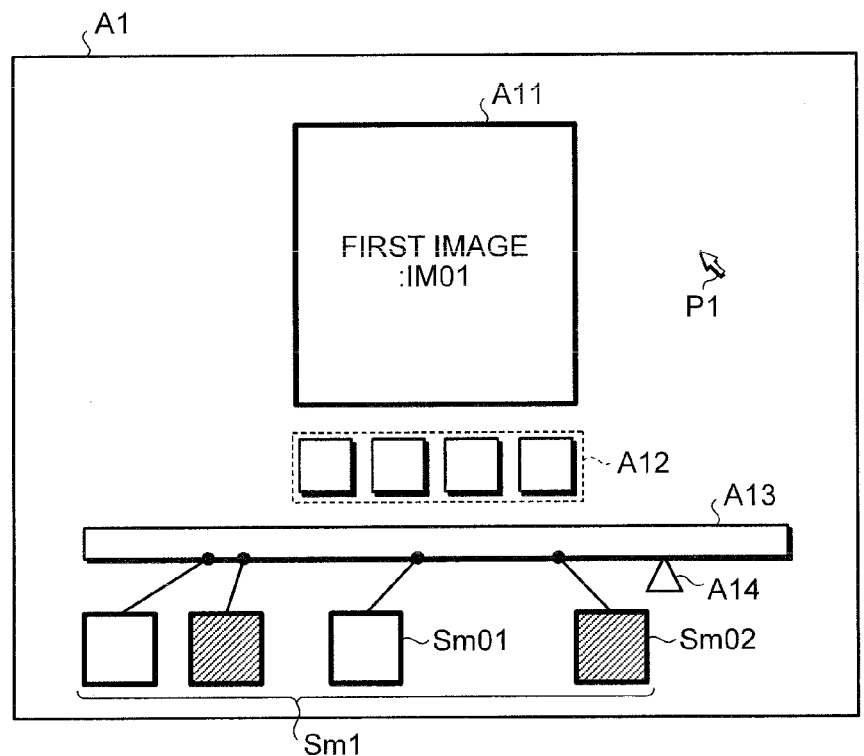
FIG. 22 is a schematic diagram illustrating an example of the display of, in the second embodiment of the present invention, a thumbnail image created from first image data and a thumbnail image created from second image data while linking them to positions on the time axis indicated by a time bar on the GUI screen.
Figure 23:
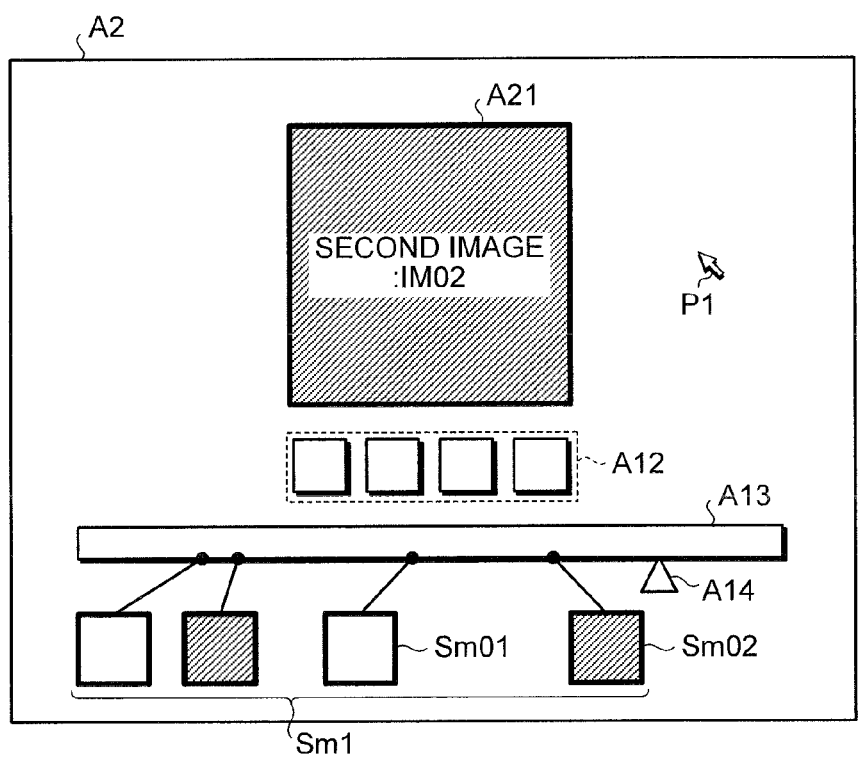
FIG. 23 is a schematic diagram illustrating an example of the display of, in the second embodiment of the present invention, the thumbnail images while linking them to positions on the time axis indicated by the time bar on the GUI screen.

In the following, examples of GUI screen displayed on the monitor 406 according to the second embodiment of the present invention will be described with reference to the drawings. FIG. 20 are schematic diagrams illustrating examples of a GUI screen A1 displaying a first image (an image created using the first image data im01) IM01, which is a normal-light image, and a GUI screen A2 displaying a second image (an image created using the second image data im02) IM02, which is a special-light image. FIG. 21 is a schematic diagram illustrating an example of a GUI screen A3 that displays, in parallel, the first image IM01 and the second image IM02. FIG. 22 is a schematic diagram illustrating an example of the display of a thumbnail image Sm01 created from the first image data im01 and a thumbnail image Sm02 created from the second image data im02 while linking them to positions on the time axis indicated by a time bar A13 on the GUI screen A1. FIG. 23 is a schematic diagram illustrating an example of the display of the thumbnail image Sm01 and the thumbnail image Sm02 while linking them to positions on the time axis indicated by the time bar A13 on the GUI screen A2.

As illustrated in FIG. 20, first, the GUI screen A1 that displays the first image IM01 that is the normal-light image includes a main-image display area A11 that displays the first image IM01; an operation button A12 that is used to input a change instruction (GUI screen change instruction) in which the GUI screen that is displayed on the monitor 406 is changed from among the GUI screens A1 to A3, which will be described later, or that is used to input a registration instruction (thumbnail registration instruction) to register the thumbnail image Sm01 (or the thumbnail image Sm02) of the first image IM01 (or the second image IM02) that is displayed in a main-image display area A11 (or a main-image display area A21, A31, or A32); a time bar A13 that indicates the time axis of an image-capturing time period during which the capsule endoscope 10 captures images (time period during which at least the first image data im01 or the second image data im02 is present); and a slider A14 that indicates the position on the time axis of the first image IM01 that is being displayed in the main-image display area A11 (or the main-image display areas A21, A31, or A32) and that is used to input a selection instruction (display image selection instruction) to change the first image IM01 (or the second image IM02) that is being displayed in the main-image display area A11. On the GUI screen A2 displaying the second image IM02 that is the special-light image, the main-image display area A11 is replaced by a main-image display area A21 that displays the second image IM02.

The GUI screen A3 illustrated in FIG. 21 includes two main-image display areas A11 and A21 that are embedded on the GUI screens A1 and A2. In these two main-image display areas A11 and A21, for example, the first image IM01 and the second image IM02 that are captured at substantially the same time are displayed.

Wile observing the first image IM01 and the second image IM02 displayed in the main-image display areas A11 and A21, by operating the operation button A12 or the slider A14 using a pointer P1 that is one of the GUI functions of the input device 411, a user inputs, via the input device 411, an operation, such as selection of images to be displayed in the main-image display areas A11 and A21, a change of a GUI screen to be displayed on the monitor 406, or registration of the thumbnail images Sm01 and Sm02 of the first image IM01 and the second image IM02 displayed in the main-image display area A11 and A21, respectively. If a user selects the thumbnail image Sm01 or Sm02, the first image IM01 or the second image IM02 corresponding to the selected thumbnail image Sm01 or Sm02 is displayed in the main-image display area A11 or A21.

With this configuration, in the second embodiment, it is possible to provide a GUI screen, to a user, in which thumbnail images of the normal-light image and the special-light image can be easily registered and viewed. Because the other configurations, operations, and advantages are the same as those described in the first embodiment or the modifications thereof, a description thereof in detail will be omitted here.

Modification 2-1

In the second embodiment described above, a case has been described, as an example, in which the thumbnail image Sm01 of the first image IM01 that is being displayed in the main-image display area A11 or the thumbnail image Sm02 of the second image IM02 that is being displayed in the main-image display area A21 is separately registered; however the present invention is not limited thereto. For example, it is also possible to automatically register, with a single thumbnail registration instruction operated by a user, the thumbnail image Sm01 or Sm02 of the first image IM01 or the second image IM02 that is being displayed in the main-image display area A11/A21 and the thumbnail image Sm02 or Sm01 of the second image IM02 or the first image IM01 that is obtained at substantially the same time when the first image IM01 or the second image IM02 is obtained. In the following, this case will be described in detail as modification 2-1 according to the second embodiment of the present invention with reference to the drawings.

Figure 24:
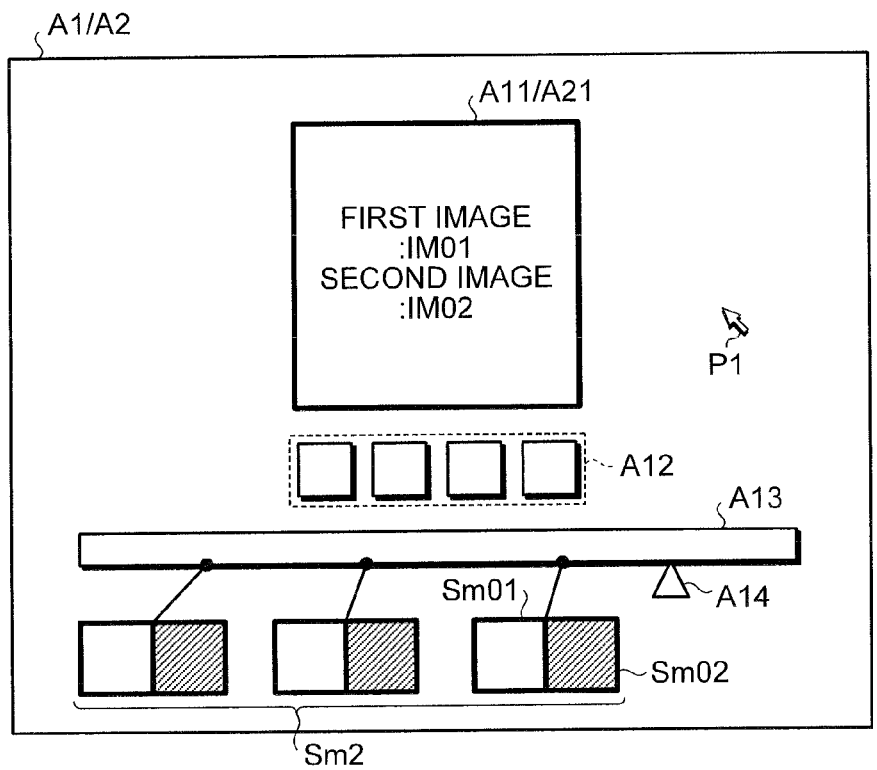
FIG. 24 is a schematic diagram illustrating an example of a GUI screen according to modification 2-1 of the second embodiment of the present invention.
Figure 25:
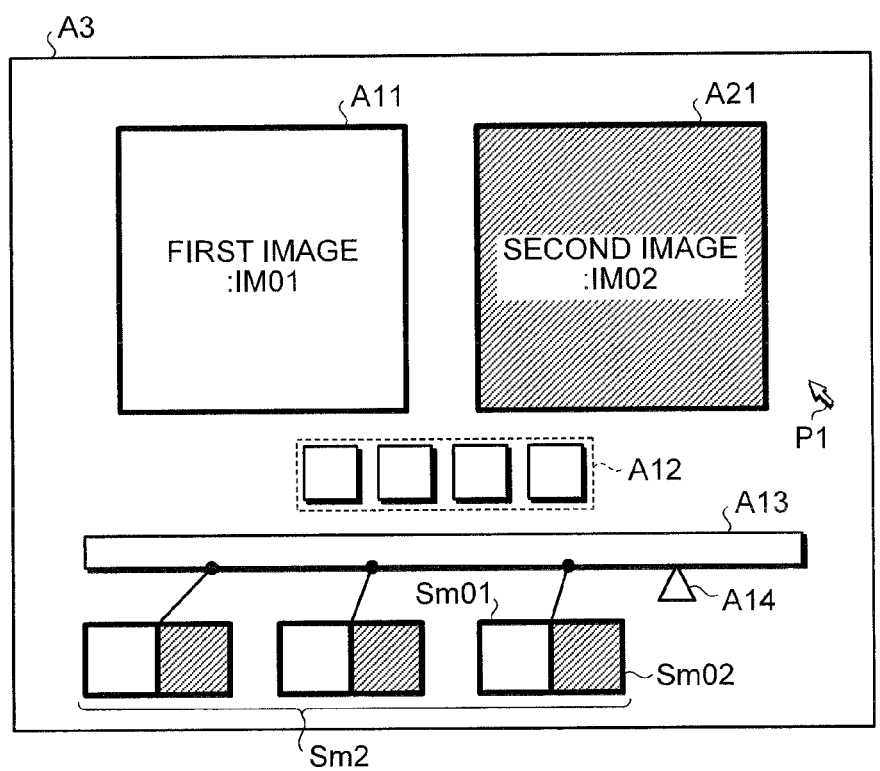
FIG. 25 is a schematic diagram illustrating an example of a GUI screen according to the modification 2-1 of the second embodiment of the present invention.

FIG. 24 is a schematic diagram illustrating an example of a GUI screen A1/A2 according to the modification 2-1 of the second embodiment of the present invention. FIG. 25 is a schematic diagram illustrating an example of a GUI screen A3 according to the modification 2-1 of the second embodiment of the present invention. As illustrated in FIG. 24, with the GUI screen A1/A2 according to the modification 2-1, for the points on the time axis indicated by the time bar A13, both the thumbnail image Sm01 of the first image IM01 and the thumbnail image Sm02 of the second image IM02 are registered. Similarly, as illustrated in FIG. 25, with the GUI screen A3 according to the modification 2-1, for the points on the time axis indicated by the time bar A13, both the thumbnail image Sm01 of the first image IM01 and the thumbnail image Sm02 of the second image IM02 are registered.

With this configuration, in the modification 2-1, by inputting a registration instruction of a thumbnail image with respect to one of the normal-light image and the special-light image, it is possible to automatically register thumbnail images in both of the images and to display them in parallel. Accordingly, it is possible to provide a GUI screen, to a user, in which thumbnail images of multiple images can be easily registered and viewed. Because the other configurations, operations, and advantages are the same as those described in the first embodiment or the modifications thereof, a description thereof in detail will be omitted here.

Third Embodiment

In the following, an in-vivo observation system and a body-insertable apparatus according to a third embodiment of the present invention will be described in detail with reference to the drawings. In the following description, elements that have the same configuration as in the first and second embodiments or in the modifications thereof are assigned the same reference numerals, and a description thereof in detail is omitted.

Figure 26:
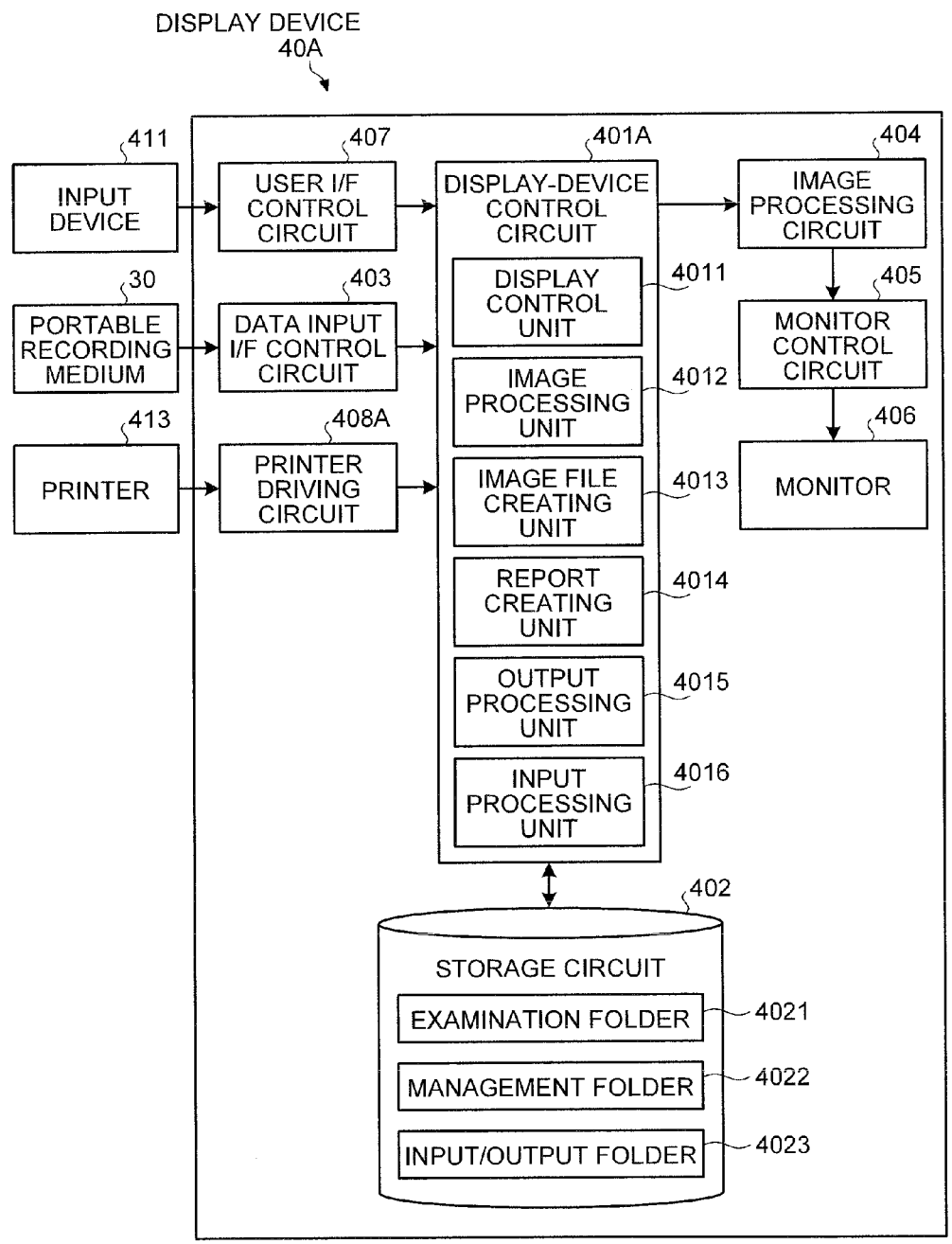
FIG. 26 is a block diagram illustrating, in outline, the configuration of a display device according to a third embodiment of the present invention.

In the third embodiment, a user can add a comment to the first image IM01 or the second image IM02 that is obtained by the capsule endoscope 10 according to the first embodiment described above. Furthermore, in the third embodiment, the first image IM01 and/or the second image IM02 including a comment can be output, in a report format, to an electronic file or sheets of paper. In the third embodiment, it is possible to use a structure similar to the capsule endoscope system 1 according to the first embodiment. However, in the third embodiment, the display device 40 illustrated in FIG. 11 is replaced by a display device 40A illustrated in FIG. 26. FIG. 26 is a block diagram illustrating, in outline, the configuration of the display device 40A according to a third embodiment of the present invention.

As illustrated in FIG. 26, the display device 40A has the same configuration as the display device 40 illustrated in FIG. 11, except that the display-device control circuit 401 is replaced by the display-device control circuit 401A and except that a printer driving circuit 408A that is connected to an external printer 413 is added. Furthermore, the storage circuit 402 stores therein an examination folder 4021, a management folder 4022, and an input/output folder 4023.

The display-device control circuit 401A includes a display control unit 4011 that controls, for example, the change of GUI screens to be displayed on the monitor 406; an image processing unit 4012 that performs a process, such as a structure enhancement process or a narrow-band-component extraction process, on the first image data im01 or the second image data im02 received from the capsule endoscope 10 in accordance with various instructions that are input from the input device 411; an image file creating unit 4013 that creates an image file of the first image data im01 or the second image data im02 that has been subjected to processing by the image processing unit 4012; a report creating unit 4014 that creates a report in which a comment (text) or the like that is input from the input device 411 is added to the image file created by the image file creating unit 4013; an output processing unit 4015 that exports the created report to an electronic file, such as a portable document format (PDF) file or sheets of paper; and an input processing unit 4016 that imports, from, for example, the storage circuit 402 or an external memory, the report that is output as an electronic file.

In the storage circuit 402, the examination folder 4021 stores therein, as a single examination file, the image data group im1 of the first image data im01 and the second image data im02 received from the capsule endoscope 10 at a single examination. The management folder 4021 stores therein, as a management file, a file containing various information, such as information on the subject 900 or examination date. The input/output folder 4023 stores therein an electronic file of a report that is created and exported by a user. Furthermore, management files and examination files can be associated with each other.

Figure 27:
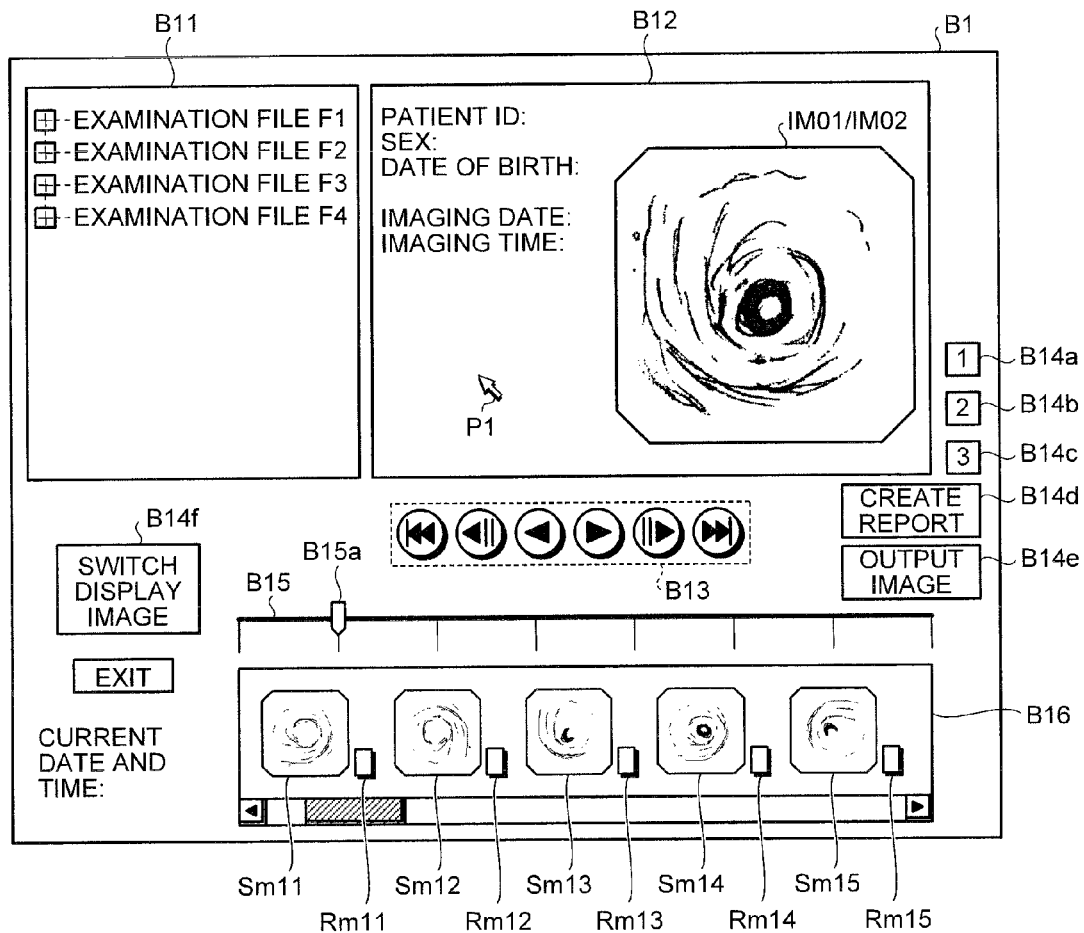
FIG. 27 is a schematic diagram illustrating, according to the third embodiment of the present invention, a GUI screen that is used by a user to check and select an examination file that is used to create a report.
Figure 28:
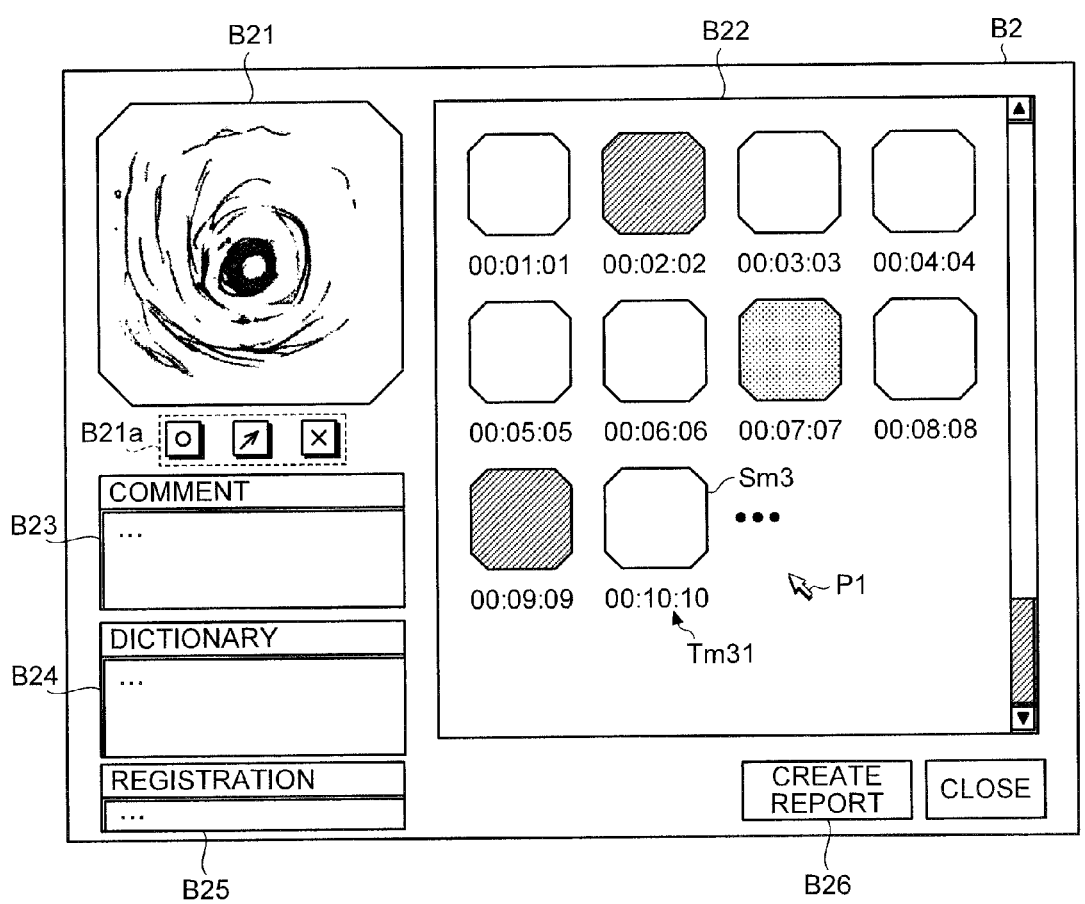
FIG. 28 is a schematic diagram illustrating a GUI screen that is used to input, for example, a comment with respect to the first image or the second image contained in the examination file selected on the GUI screen illustrated in FIG. 27.
Figure 29:
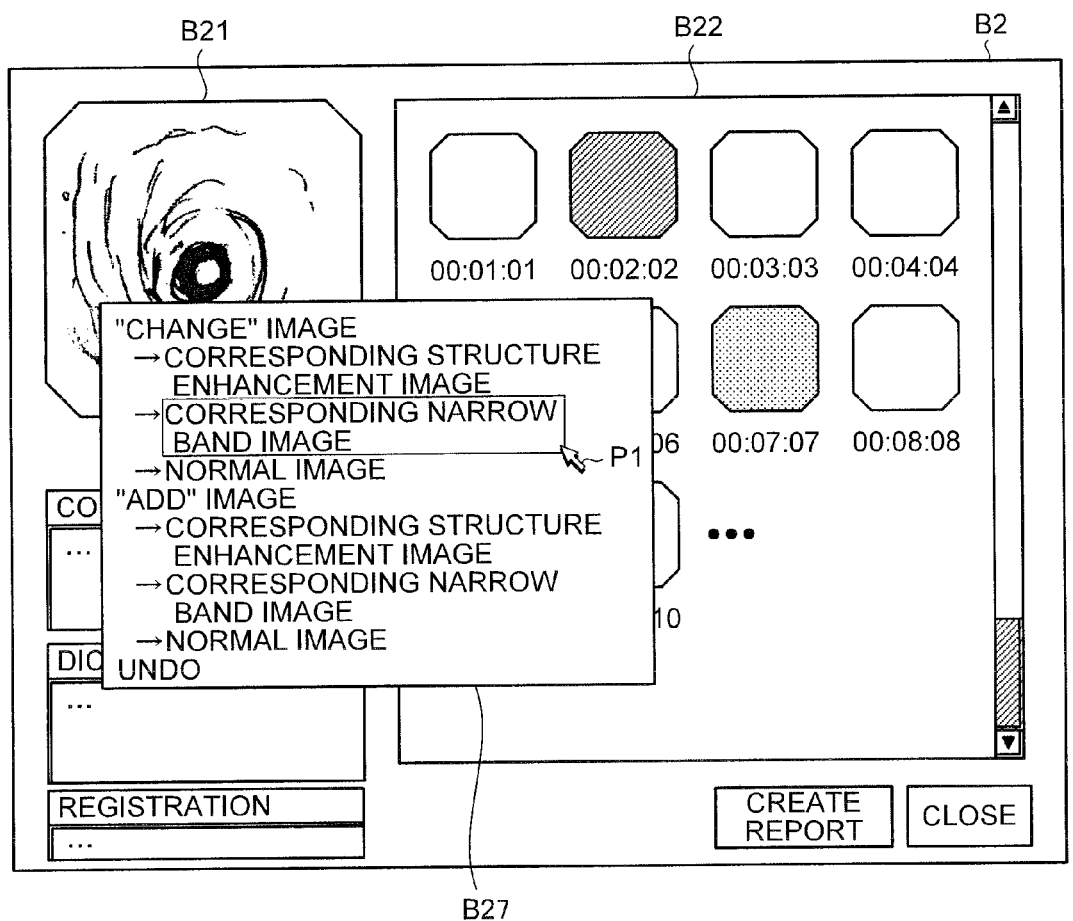
FIG. 29 is a schematic diagram illustrating, using the GUI screen illustrated in FIG. 28, the operation performed when a user instructs image processing, such as a structure enhancement process or a narrow-band-component extraction process.
Figure 30:
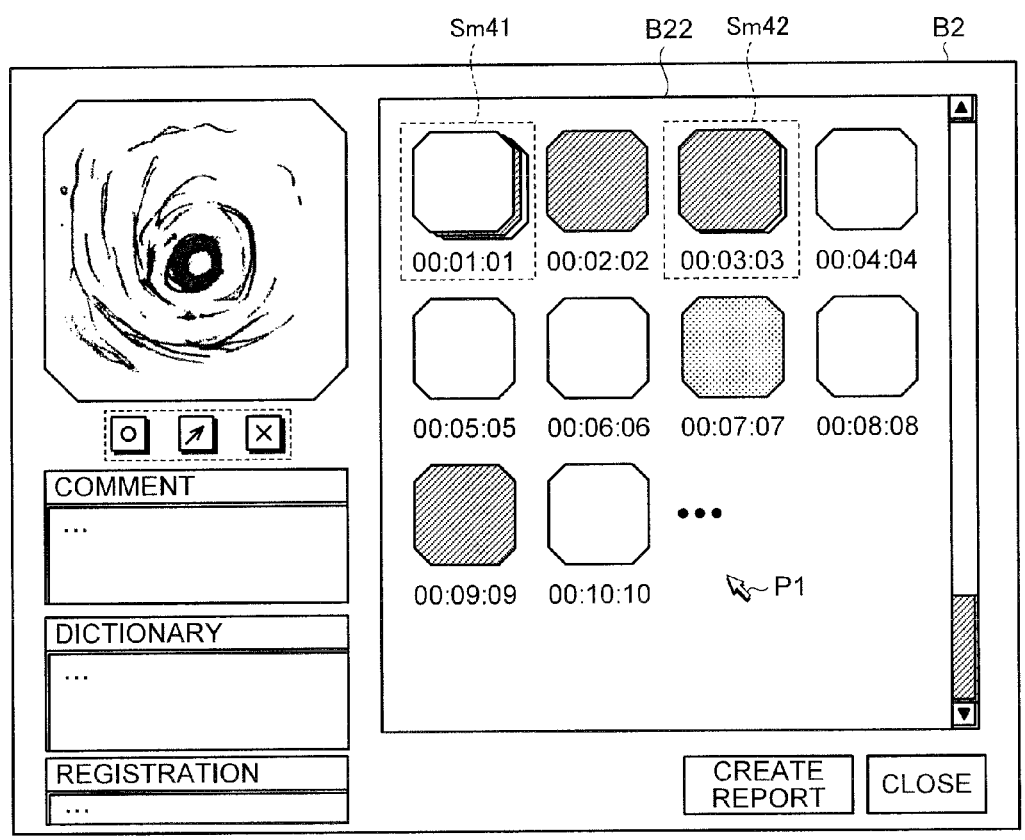
FIG. 30 is a schematic diagram illustrating, according to the third embodiment of the present invention, an example of a screen of a thumbnail image of the first image or the second image that contains an image that has been subjected to processing, such as the structure enhancement process or the narrow-band-component extraction process.

In the following, a GUI screen that is used to create a report and a report that is created using this GUI screen according to the third embodiment will be described with reference to the drawings. FIG. 27 is a schematic diagram illustrating, according to the third embodiment of the present invention, a GUI screen B1 that is used by a user to check and select an examination file that is used to create a report. FIG. 28 is a schematic diagram illustrating a GUI screen B2 that is used to input, for example, a comment with respect to the first image IM01 or the second image IM02 contained in the examination file selected on the GUI screen B1 illustrated in FIG. 27. FIG. 29 is a schematic diagram illustrating, using the GUI screen B2 illustrated in FIG. 28, the operation performed when a user instructs image processing, such as a structure enhancement process or a narrow-band-component extraction process. FIG. 30 is a schematic diagram illustrating, according to the third embodiment of the present invention, an example of a screen of thumbnail images of the first image IM01 or the second image IM02 containing an image that has been subjected to processing, such as the structure enhancement process or the narrow-band-component extraction process.

As illustrated in FIG. 27, the GUI screen B1 includes a target-examination file-list display field B11 that is used to display, in a selectable manner, a list of examination files F1 to F4 that are used to create a report; a main display area B12 that is used to display either one of the first image IM01 and the second image IM02 contained in the selected examination file or that is used to display information on the subject 900 or the like; an operation button B13 that switches the first image IM01 and the second image IM02 of a still image displayed in the main display area B12 or that is used to input an operation, such as a forward replay, a reverse replay, fast forward, rewind, and search, in order to replay the first image IM01 or the second image IM02 of a moving image on the main display area B12; switching buttons B14a to B14c that switch, the number of first images IM01 or second images IM02 displayed in the main display area B12 at a time from among, for example, one, two, and four; a report creating button B14d that is used to input an instruction to create a report with respect to the first image IM01 or the second image IM02 displayed in the main display area B12; an image output button B14e that is used to input an instruction to print the first image IM01 or the second image IM02; a display-image switching button B14f that switch either one of the first image IM01 and the second image IM02 displayed in the main display area B12; a time bar B15 that indicates the time axis of an image-capturing time period during which the capsule endoscope 10 captures images (time period during which at least the first image data im01 or the second image data im02 is present; a slider B15a that indicates the position on the time axis of the first image IM01 or the second image IM02 that is being displayed in the main display area B12, and that is used to input a change instruction (display image selection instruction) to change the first image IM01 or the second image IM02 that is being displayed in the main display area B12; and a sub display area B16 in which registered thumbnail images Sm11 to Sm15 . . . are displayed in chronological order. Furthermore, comment flags Rm11 to Rm15 . . . , which indicate whether a comment is added to the first image data im01 or the second image data im02 associated with each thumbnail image, are displayed close to each of the thumbnail images Sm11 to Sm15, . . . displayed in the sub display area B16.

On the GUI screen B1 displayed on the monitor 406, using the pointer P1 via the input device 411, a user selects one of the examination files F1 to F4 that corresponds to the target file for creating a report. Images in the examination file can be checked by referring to the first image IM01 or the second image IM02 that is displayed in the main display area B12 or referring to the thumbnail images Sm11 to SM15, . . . that are displayed in the sub display area B16. If a user clicks the report creating button B14d while selecting one of the examination files, the GUI screen B2 illustrated in FIG. 28 is displayed on the monitor 406.

As illustrated in FIG. 28, the GUI screen B2 includes a target image display area B21 that displays an image to which a comment is input between the first image IM01 and the second image IM02 contained in the examination file (here, an examination file F1 is used) that is the target file for creating a report; a comment input field B23 that is used to input a comment added to the first image IM01 or the second image IM02 that is being displayed in the target image display area B21; an edit button B21a that is used to add the comment that is input to the comment input field B23 to the first image IM01 or the second image IM02 to be subjected or that is used to delete the comment that is added to the first image IM01 or the second image IM02 to be subjected; a dictionary field B24 that is used to display, for example, general information related to the first image IM01 or the second image IM02 that is being displayed in the target image display area B21; a dictionary registration field B25 that is used to input the general information registered in the dictionary field; a thumbnail list display area B22 that is used to display thumbnail images Sm11 to Sm15 . . . that are registered in the first image IM01 and the second image IM02 in the examination file F1 in a list form; and a report creating button B26 that is used to print or export the report on the first image IM01 or the second image IM02 to which a comment is added. Furthermore, time information Tm31 that indicates an image-capturing time of each of the first image data im01 and the second image data im02 and that is associated with each thumbnail image Sm3 displayed in the thumbnail list display area B22 can also be displayed close to each thumbnail image Sm3.

On the GUI screen B2 displayed on the monitor 406, using the pointer P1 via the input device 411, a user selects one of the thumbnail images Sm3 displayed in the thumbnail list display area B22. By doing so, the first image IM01 or the second image IM02 that is associated with the selected thumbnail image Sm3 is displayed in the target image display area B21. In this state, by using, for example, a keyboard included in the input device 411, a user inputs a comment in the comment input field B23 and clicks a registration button arranged at the edit button B21a, whereby the input comment is added to the first image IM01 or the second image IM02 that is selected. Furthermore, by using the pointer P1 via the input device 411, a user clicks the report creating button B26, whereby a report R1 or R2 like that illustrated in FIG. 31A or 31B, respectively, is created.

Furthermore, if a user clicks, for example, the right mouse button included in the input device 411 with respect to the first image IM01 or the second image IM02 displayed in the target image display area B21, a processing menu field B27 like that illustrated in FIG. 29 is displayed in a pop-up window on the GUI screen B2. By using the pointer P1 via the input device 411, a user selects one of the processing options displayed in the processing menu field B27, whereby processing is performed on the first image data im01 or the second image data im02 to be subjected.

If the first image data im01 or the second image data im02 that is being selected is subjected to processing to create image data, regarding thumbnail images (hereinafter, referred to as "thumbnail images Sm41") in the thumbnail list display area B22 on the GUI screen B2 corresponding to the image data, as illustrated in FIG. 30, the thumbnail images of the processed image data are superimposed. Accordingly, a user can easily specify the processed image data contained in either one of the first image IM01 and the second image IM02. In the thumbnail list display area B22, it is also possible to display, in a superimposed manner, thumbnail images of the first image data im01 and the second image data im02 that are obtained at the same time. By doing so, a user can easily specify an image in which both a normal-light image and a special-light image are present.

Figure 31A:
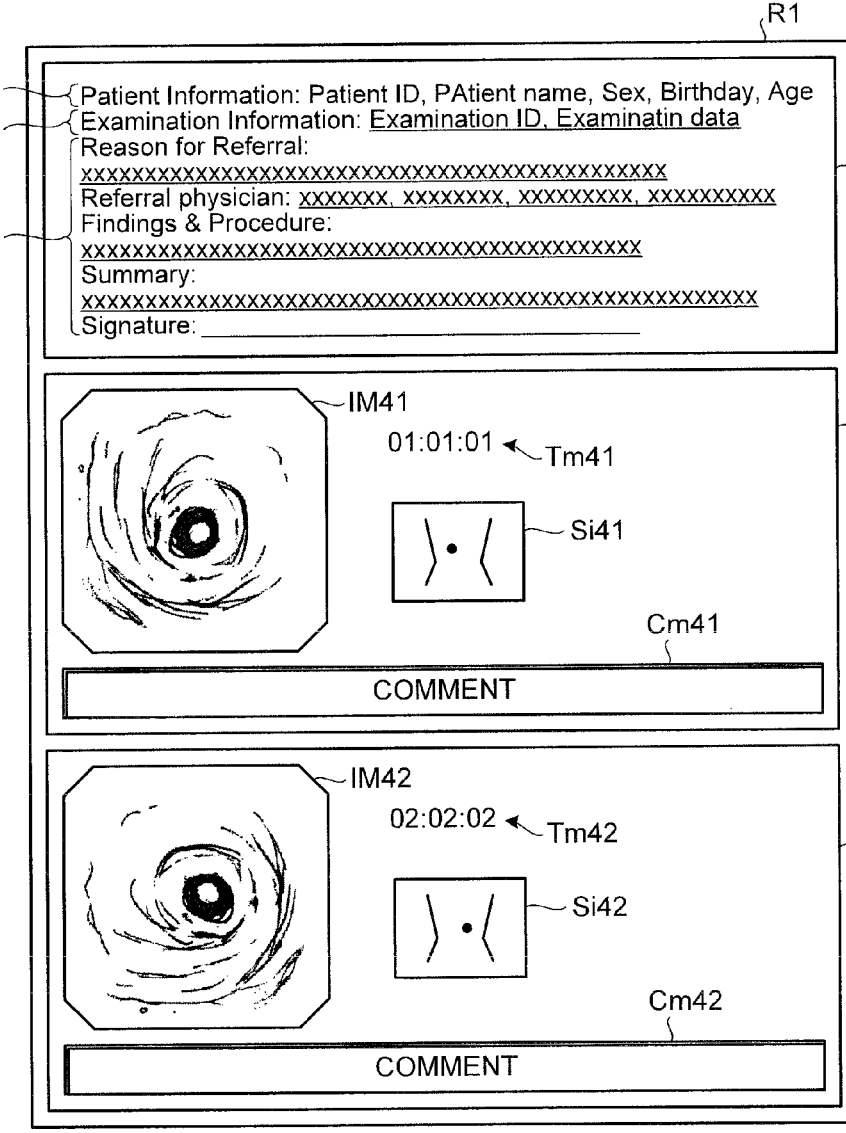
FIG. 31A is a schematic diagram illustrating an example of a report that is created and exported using the GUI screen according to the third embodiment of the present invention (No. 1)
Figure 31B:
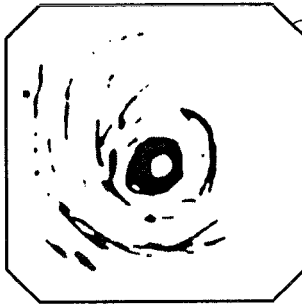
FIG. 31B is a schematic diagram illustrating an example of a report that is created and exported using the GUI screen according to the third embodiment of the present invention (No. 2)

In the following, an example of a report that is created and exported using the GUI screens B1 and B2 will be described in detail with reference to the drawings. FIGS. 31A and 31B are schematic diagrams illustrating examples of reports that are created and exported using the GUI screens B1 and B2 illustrated in FIGS. 27 to 30.

As illustrated in FIG. 31A, the report R1 includes a header region R41 that is used to display various information, such as information on the subject 900 (patient information R41a), examination information R41b, and information on findings and treatment procedures (diagnosis information R41c). The report R1 also includes a body regions R42A and R42B that is used to display images IM41 and IM42 to which comments Cm41 and Cm42 are added, respectively; image-capturing times Tm41 and Tm42 of the images IM41 and IM42, respectively; images Si41 and Si42 that indicate image-capturing location inside the subject 900 for the images IM41 and IM42, respectively; and comments Cm41 and Cm42 added to the images IM41 and IM42, respectively. The number of body regions is not limited to two; one body region or three or more body regions can also be used.

As illustrated in FIG. 31B, the structure of the report R2 can also be configured to display, for an image IM51 that has been subjected to processing, a comment (see a body region R52A), or to display, for a plurality of images IM42 and IM52, a single comment (see a body region R52B).

Figure 32:
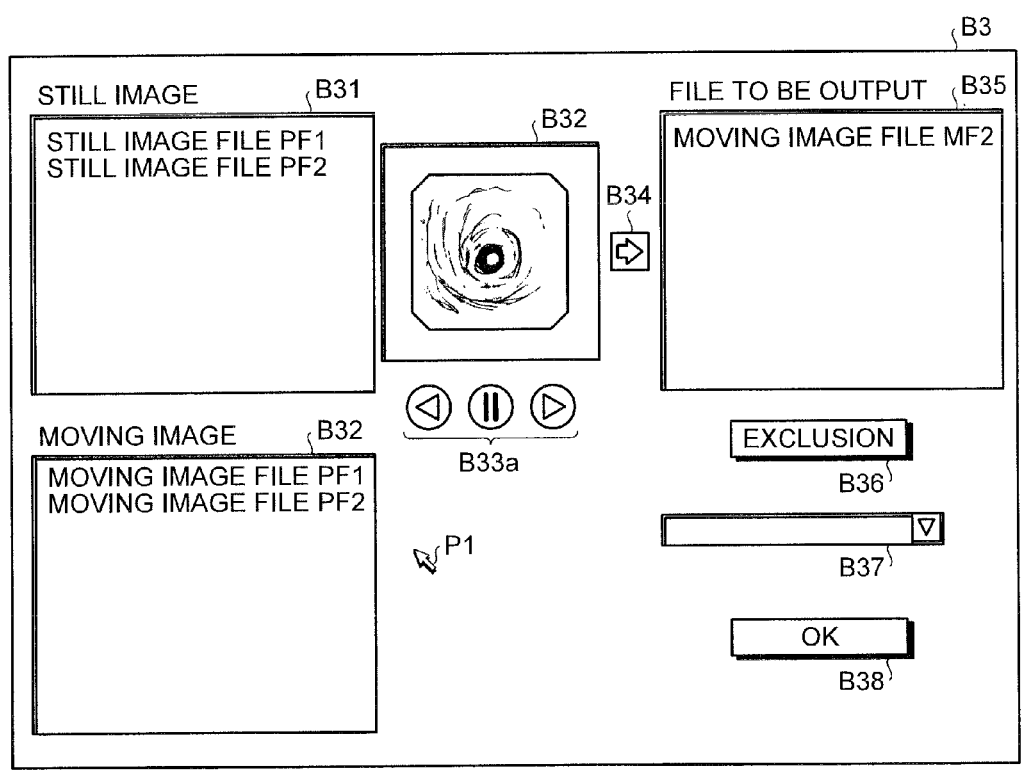
FIG. 32 is a schematic diagram illustrating an example of a GUI screen that is used to output, as a single file, at least one of the image files if the examination files according to the third embodiment of the present invention contains multiple image files.

Furthermore, as illustrated in FIG. 32, if a plurality of files, such as still images (still image files PF1, PF2, . . . ) or moving images (moving image file MF1, MF2, . . . ) are present in the first image data im01 or the second image data im02, it is also possible to configure such that at least one of the files can be output as a single file. FIG. 32 is a schematic diagram illustrating an example of a GUI screen B3 that is used to output, as a single file, at least one of the image files if the examination files F1 to F4, . . . contains multiple image files.

For example, on the GUI screen B3 illustrated in FIG. 32, if the still image file PF1 or PF2 is output as a single file or if the moving image file MF1 or MF2 is output as a single file, using the pointer P1 included in the input device 411, a user selects, from a still image list B31 or a moving image list B32, a target file (the moving image file MF2 in the example illustrated in FIG. 32) and clicks a registration button B34. By doing so, the selected file (moving image file MF2) is registered in a list B35 of the file that is output as a single file. Furthermore, the selected file is replayed in, for example, a replay field B33. The available replay operation in the replay field B33 includes pause, forward replay, and backward replay using an operation button B33a. If a user clicks an exclusion button B36 while selecting one of the files listed in the list B35 on the GUI screen B3, the file that is being selected is excluded from the file to be output. Furthermore, if a user clicks an OK button B38, one or more files registered in the list B35 is output as a single file. A name that is input to a name input field B37 by, for example, a user using the input device 411 can be used for the name of the output file.

Figure 33:
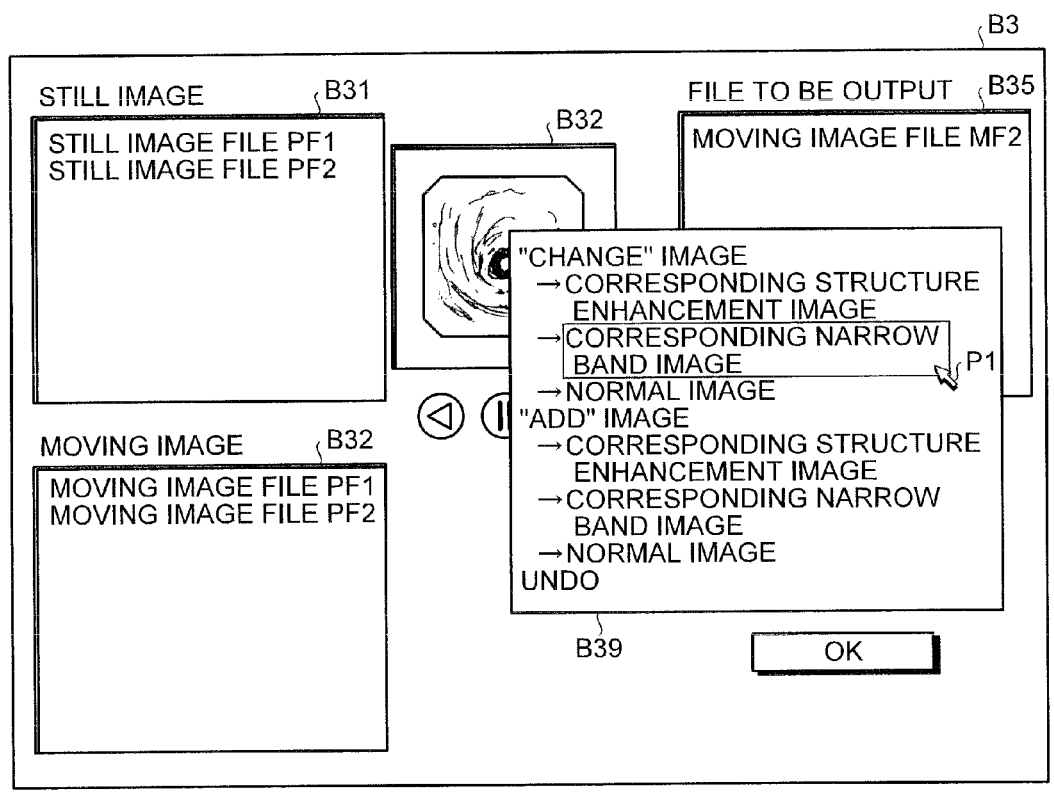
FIG. 33 is a schematic diagram illustrating the operation performed when a user instructs processing, such as the structure enhancement or the narrow-band-component extraction process, with respect to image data of the image displayed on a replay field on the GUI screen illustrated in FIG. 32.

FIG. 33 is a schematic diagram illustrating the operation performed when a user instructs processing, such as the structure enhancement or the narrow-band-component extraction process, with respect to image data of the image displayed on a replay field B33 on the GUI screen B3 illustrated in FIG. 32.

If a user clicks, for example, the right mouse button included in the input device 411 with respect to the image displayed in the replay field B33, a processing menu field B39 like that illustrated in FIG. 33 is displayed in a pop-up window on the GUI screen B3. By using the pointer P1 via the input device 411, a user selects one of the processing options displayed in the processing menu field B39, whereby processing is performed on the image data of the image that is being displayed. The image data that has been subjected to the processing is newly registered in the still image list B31 or the moving image list B32 as a still image file or a moving image file, respectively.

With this configuration described above, in the third embodiment, it is possible to easily and definitely add a comment to a target image or a target image group (examination file) and output it as a report. Because the other configurations, operations, and advantages are the same as those described in the first embodiment or the modifications thereof, a description thereof in detail will be omitted here.

According to the embodiments of the present invention, in addition to a light source for obtaining a normal-light image, a light source for obtaining a special-light image is additionally arranged, and both the normal-light image and the special-light image while driving these light sources in combination. Accordingly, it is possible to implement an in-vivo image-capturing system and a body-insertable apparatus capable of obtaining the normal-light image and the special-light image without increasing the burden imposed on the image processing.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An in-vivo image-capturing system, comprising:
 a body-insertable apparatus that is introduced into a subject; and
 a receiving device that receives a wireless signal transmitted from the body-insertable apparatus, wherein
 the body-insertable apparatus includes
  a light-receiving unit that includes a plurality of light-receiving elements having a receiving wavelength spectrum for receiving red, blue, and green light, respectively,
  a plurality of light-emitting units having a plurality of emission wavelength spectra respectively deviated from a center wavelength of the receiving wavelength spectrum by a predetermined wavelength, the light-emitting units including a near ultraviolet light source whose peak of the emission intensity is near ultraviolet light, a yellow light source whose peak of the emission intensity is yellow, a cyan light source whose peak of the emission intensity is cyan, and a near infrared light source whose peak of the emission intensity is near infrared light, and a selection unit that can select, from among the light-emitting units, a light-emitting unit corresponding to the near ultraviolet light source and a light-emitting unit corresponding to the yellow light source, wherein a B pixel of one of the light-receiving elements for receiving blue-color-component light has a peak of a receiving intensity at a wavelength that is closer to an ultraviolet light side than to a wavelength indicating the peak of the emission intensity of the cyan light source, and the B pixel has a spectral sensitivity characteristic to the near ultraviolet light, a G pixel of one of the light-receiving elements for receiving green-color-component light has a peak of a receiving intensity at a wavelength that is located between a wavelength indicating the peak of the emission intensity of the cyan light source and a wavelength indicating the peak of the emission intensity of the yellow light source, and an R pixel of one of the light-receiving elements for receiving red-color-component light has a peak of a receiving intensity at a wavelength that is located between a wavelength indicating the peak of the emission intensity of the yellow light source and a wavelength indicating the peak of the emission intensity of the near infrared light source, and wherein the body-insertable apparatus further includes an image creating unit that creates a normal-light image in accordance with a combined flat-shaped wavelength spectrum received by all the light-receiving elements for receiving red, blue, and green light when all the light-emitting units emit light and that creates a special-light image in accordance with a combined sharp wavelength spectrum combined using the B pixel that receives blue-color-component light of the light-receiving unit and the G pixel that receives green-color-component light of the light-receiving unit, the light being obtained at the emission of light when the near ultraviolet light source and the yellow light source are selected using the selection unit, a transmitting unit that transmits the normal-light image or the special-light image created by the image creating unit, and a control unit that controls driving of the light-receiving elements in accordance with selection performed by the selection unit.

2. The in-vivo image-capturing system according to claim 1, wherein the transmitting unit individually transmits the normal-light image and the special-light image.

3. The in-vivo image-capturing system according to claim 1, wherein by driving the light-emitting unit and the light-receiving unit, the control unit alternately allows the normal-light image and the special-light image to be created, the light-receiving unit includes a buffer memory that temporarily stores therein the normal-light image or the special-light image, and the transmitting unit continuously transmits the special-light image or the normal-light image that is created by the light-receiving unit and the normal-light image or the special-light image that is stored in the buffer memory.

4. The in-vivo image-capturing system according to claim 1, wherein light other than light of the emission wavelength spectrum near the near ultraviolet light region is created by shifting wavelengths of light of the emission wavelength spectrum near the near ultraviolet light region.

5. The in-vivo image-capturing system according to claim 1, wherein the emission wavelength spectra include an emission wavelength spectrum of a blue wavelength band, an emission wavelength spectrum of a green wavelength band, and an emission wavelength spectrum of a red wavelength band.

6. The in-vivo image-capturing system according to claim 1, wherein the emission wavelength spectrum near the near ultraviolet light region is sharper than emission wavelength spectra that are other than the emission wavelength spectrum near the near ultraviolet light region.

7. A body-insertable apparatus comprising:

a light-receiving unit that includes a plurality of light-receiving elements having a receiving wavelength spectrum for receiving red, blue, and green light, respectively;

a plurality of light-emitting units having a plurality of emission wavelength spectra respectively deviated from a center wavelength of the receiving wavelength spectrum by a predetermined wavelength, the light-emitting units including a near ultraviolet light source whose peak of the emission intensity is near ultraviolet light, a yellow light source whose peak of the emission intensity is yellow, a cyan light source whose peak of the emission intensity is cyan, and a near infrared light source whose peak of the emission intensity is near infrared light, and;

a selection unit that can select, from among the light-emitting units, a light-emitting unit corresponding to the near ultraviolet light source and a light-emitting unit corresponding to the yellow light source, wherein a B pixel of one of the light-receiving elements for receiving blue-color-component light has a peak of a receiving intensity at a wavelength that is closer to an ultraviolet light side than to a wavelength indicating the peak of the emission intensity of the cyan light source, and the B pixel has a spectral sensitivity characteristic to the near ultraviolet light, a G pixel of one of the light-receiving elements for receiving green-color-component light has a peak of a receiving intensity at a wavelength that is located between a wavelength indicating the peak of the emission intensity of the cyan light source and a wavelength indicating the peak of the emission intensity of the yellow light source, and an R pixel of one of the light-receiving elements for receiving red-color-component light has a peak of a receiving intensity at a wavelength that is located between a wavelength indicating the peak of the emission intensity of the yellow light source and a wavelength indicating the peak of the emission intensity of the near infrared light source, and wherein the body-insertable apparatus further includes an image creating unit that creates a normal-light image in accordance with a combined flat-shaped wavelength spectrum received by all the light-receiving elements for receiving red, blue, and green light when all the light-emitting units emit light and that creates a special-light image in accordance with a combined sharp wavelength spectrum combined using the B pixel that receives blue-color-component light of the light-receiving unit and the G pixel that receives green-color-component light of the light-receiving unit, the light being obtained at the emission of light when the near ultraviolet light source and the yellow light source are selected using the selection unit;

a transmitting unit that transmits the normal-light image or the special-light image created by the image creating unit; and
a control unit that controls driving of the light-receiving elements in accordance with selection performed by the selection unit.

* * * * *